(12) United States Patent
Brown et al.

(10) Patent No.: US 7,056,515 B2
(45) Date of Patent: Jun. 6, 2006

(54) ANTIGENS FOR IMMUNOCONTRACEPTION

(75) Inventors: Robert George Brown, Dartmouth (CA); Marc Mansour, Halifax (CA); Bill Pohajdak, Dartmouth (CA)

(73) Assignee: Immunovaccine Technologies Inc., Halifax (CA)

( * ) Notice: Subject to any disclaimer, the term of this patent is extended or adjusted under 35 U.S.C. 154(b) by 0 days.

(21) Appl. No.: 10/636,620

(22) Filed: Aug. 8, 2003

(65) Prior Publication Data
US 2004/0202674 A1 Oct. 14, 2004

Related U.S. Application Data

(63) Continuation-in-part of application No. PCT/CA03/00177, filed on Feb. 10, 2003.

(60) Provisional application No. 60/380,293, filed on May 15, 2002, provisional application No. 60/354,525, filed on Feb. 8, 2002.

(51) Int. Cl.
*A61K 39/00* (2006.01)
(52) U.S. Cl. ................ 424/185.1; 530/350; 514/12
(58) Field of Classification Search .............. 530/350; 435/7.1, 69.1; 424/185.1
See application file for complete search history.

(56) References Cited

U.S. PATENT DOCUMENTS 5,837,497 A * 11/1998 Harris ................ 435/69.3
6,001,599 A 12/1999 Harris et al.
6,027,727 A 2/2000 Harris et al.
RE37,224 E 6/2001 Brown et al.

FOREIGN PATENT DOCUMENTS

WO 9411019 5/1994
WO 03/066680 A2 8/2003

OTHER PUBLICATIONS

Kennith Woods and Thomas Hopp, Prediction of protein antigenic determinants form amino acid sequences, Jun. 1981, PNAS, vol. 78, No, pp. 3824-3828.*
Bradley, M.P. et al., "*Vaccines for fertility regulation of wild and domestic species*", J. Biotechnology 1999, vol. 73, pp. 91-101.
Brown, R.G. et al., "*Evidence for a long-lasting single administration contraceptive vaccine in wild grey seals*", J. Reprod. Immunol. 1997, vol. 35, pp. 43-51.
Brown, R.G. et al., "*Temporal trends in antibody production in captive grey, harp and hooded seals to a single administration immunocontraceptive vaccine*" J. Reprod. Immunol. 1997, vol. 35, pp. 53-64.
Fraker, M.A. et al., "*Long-lasting, single dose immunocontraception of feral fallow deer in British Columbia.*" J. Wildl. Management 2002, vol. 66, pp. 1141-1147.

(Continued)

*Primary Examiner*—Jon Weber
*Assistant Examiner*—Robert B. Mondesi

(57) ABSTRACT

The present invention provides immunocontraceptive vaccines comprising a zona pellucida (ZP) polypeptide, and/or a variant thereof, from a carnivorous mammal such as cat, dog, ferret or mink. Such vaccines are useful in reducing fertility of cats and/or dogs.

19 Claims, 14 Drawing Sheets

OTHER PUBLICATIONS

Gorman, S.P. et al. "*Evaluation of a porcine zona pellucida vaccine for the immunocontraception of domestic kittens (Felis catus)*", Theriogenology 2002, vol. 58, pp. 135-149.

Harlow, E. et al. "*Antibodies—A Laboratory Manual*" Cold Spring Harbor Laboratory, USA 1988, pp. 96-101.

Ivanova, M. et al., "*Contraceptive potential of porcine zona pellucida in cats*", Theriogenology 1995, vol. 43, pp. 969-981.

Oogjes, G. et al. "*Ethical aspects and dilemmas of fertility control of unwanted wildlife: an animal welfarist's perspective*", Reprod. Fertil. Dev. 1997, vol. 9, pp. 163-167.

Muller, L.I., et al. "*Theory and practice of immunocontraception in wild mammals*", Wildl. Soc. Bull. 1997, vol. 25, pp. 504-514.

Neville, P.F. et al., "*Feral cats: management of urban populations and pest problems by neutering*", In Putman R.J. (ED): Mammals as pests. London, Chapman & Hall 1989, pp. 261-267.

Neville, P.F. et al., "*Effect of neutering on two groups of feral cats*", Vet. Rec 1984, vol. 114, pp. 447-450.

Oogjes, G. et al. "*Ethical aspects and dilemmas of fertility control of unwanted wildlife: an animal welfarist's perspective*" Reprod. Fertil. Dev. 1997, vol. 9, pp. 163-167.

Page R.J.C. et al. "*A study of the home ranges, movements, and behaviour of the feral cat poopulation at avonmouth docks*", Wildlife Research 1992, vol. 19, pp. 263-277.

Remfry, J. "*Control of feral cat populations by long-term administration of megestrol acetate*", Vet. Rec. 1978, vol. 103, pp. 403-404.

Sacco, A.G. et al. "*Use of the zona pellucida as an immunocontraceptive target antigen*" In Dietl, J. (ED): The mammalian egg coat: structure and function. Berlin, Spinger-Verlag 1989, pp. 128-153.

Smith R.E. et al., "*The potential for the control of feral cat populations by neutering*" Feline Practice 1986, vol. 16, pp. 21-23.

Willis, P., et al., "*Equine immunocontraception using porcine zona pellucida: a method for remote delivery and characterization of the immune response*", J. Equine Vet. Sci. 1994, vol. 14, pp. 364-370.

Zaunbrecher, K.I. et al. "*Neutering of feral cats as an alternative to eradiction programs*" J. Am. Vet. Med. Assoc. 1993, vol. 203, pp. 449-452.

Blackmore, D. G. et al., "Biosynthesis of the canine zona pellucida requires the integrated participation of both oocytes and granulosa cells", Biol. Reprod. Aug. 2004 (Epub Apr. 28, 2004), vol. 71, No. 2, pp. 661-668, p. 664 (top right column) and Figure 4.

Fayrer-Hosken, R. A. et al., "Immunocontrol in dogs", Anim. Reprod. Sci., Jul. 2, 2000, vol. 60-61, pp. 365-373.

Harris, J. D. et al., "Cloning and characterization of zona pellucida genes and cDNAs from a variety of mammalian species: the ZPA, ZPB and ZPC gene families", DNA Seq. 1994, vol. 4, No. 6, pp. 361-393, pp. 374-375 and Figure 7.

Rath, A. et al., "Characterization of immune response in mice to plasmid DNA encoding dog zona pellucida glycoprotein-3", Vaccine, May 16, 2003, vol. 21, No. 17-18, pp. 1913-1923.

\* cited by examiner

CLUSTAL W (1.74) multiple sequence alignment

```
        ZP B1
cow*   MWLLIQLVWLCFLLSLGLNSWHQSKVPEYPDELRCGLRSFQFTINPLSQETETPPVLVAW
pig*   MWLR-PSIWLCFPLCLAIPGQSQPKAADDLGGLYCGPSSFHFSINLLSQDTATPPALVVW
cat*   MWLL--QPLLLCVPLSLAVHGQQKPQVPDYPGELHCGLQSLQFAINP-SPGKATP-ALIVW
       ***    : **. *.*.:  .  | :.:..  . * *|* *::*:**  *  . ** .*:.*
                              ?
cow*   DNHGLPHSLQNDSDCGTWVSEGPGSSLVGEASYSGCYVTEW-------------------
pig*   DRRGRLHKLQNDSGCGTWVHKGPGSSMGVEASYRGCYVTEW-------------------
cat*   DNRGLPHKLQNNSGCGTWVRESPGGSVLLDASYSSCYVNEWVSTTQSPGTSRPPTPASRV
       *.:* *.***:*|.***** :.**.*:  :***  .***.**
                                                              ZP B2
cow*   ---ESYYIMTVGIERAGVSGSGAFIETKLFKCPVNLP---------------DVPNA
pig*   ---DSHYLMPIGLEEADAGGHRTVTETKLFKCPVDFLA---------------LDVPTI
cat*   TPQDSHYVMIVGVEGTDAAG-RRVTNTKVLRCPRNPPDQALVSSLSPSPLQNVALEAPNA
       :*:*:* :*:* :...* .  :**:::** :               :  .*.
                                                  ?
cow*   GLCDSVPVWDRLPCAPSPITQGDCKQLGCCYNSEEVISCYYGNTVTSHCTQDGHFSIAVS
pig*   GLCDAVPVWDRLPCAPPPITQGECKQLGCCYNSEEVPSCYYGNTVTSRCTQDGHFSIAVS
cat*   DLCDSVPKWDRLPCASSPITQGDCNKLGCCYKS-EANSCYYGNTVTSRCTQDGHFSIAVS
       .***:** |******..|******:|*::*****:  *. ***********:*********|*****
            ZPA S1
cow*   RNVTSPPLLLNSVHLAFRNDSECKPVMATHTFVLFRFPFTTCGTTKQITGKQAVYENELV
pig*   RNVTSPPLLWDSVHLAFRNDSECKPVMETHTFVLFRFPFSSCGTAKRVTGNQAVYENELV
cat*   RNVTSPPLLLNSLRLAFGKDRECNPVKATRAFALFFFPFNSCGTTRWVTGDQAVYENELV
       ********* :*:.*** :* **:** *:.** ***:**.***:: :**.**********
            ?
cow*   AARDVRTWSRGSITRDSTFRLQVSCSYSASSSALPVNVQVLTLPPPLPETQPGNLTLELK
pig*   AARDVRTWSHGSITRDSIFRLRVSCIYSVSSSALPVNIQVFTLPPPLPETHPGPLTLELQ
cat*   AARDVRTWSHGSITRDSIFRLRVSCSYSVRSNAFPLSVQVFTIPPPHLKTQHGPLTLELK
       *********:*******:***:***.**: *.*:.:**:*::***.::*:* *****:
                                ZPB 3        ZPA S2
cow*   IAKDKRYRSYYTASDYPVVKLLRDPIYVEVSIHQRTDPSLELRLDQCWATPGADALLQPQ
pig*   IAKDERYGSYYNASDYPVVKLLREPIYVEVSIRHRTDPSLGLHLHQCWATPGMSPLLQPQ
cat*   IAKDKHYGSYYTIGDYPVVKLLRDPIYVEVSIRHRTDPSLGLLLHNCWATPGKNSQSLSQ
       ****:.:* ***. .*:*:******:****:***:*****.*  * *:****** ..  .*
            ?
cow*   WPLLVNGCPYTGDNYQTKLIPVWEASDLPFPSHYQRFSISTFSFVDSVAKRALKGPVYLH
pig*   WPMLVNGCPYTGDNYQTKLIPVQKASNLLFPSHYQRFSVSTFSFVDSVAKQALKGPVYLH
cat*   WPILVKGCPYVGDNYQTQLIPVQKALDTPFPSYYKRFSIFTFSFVDTMAKWALRGPVYLH
       **:**:***|*.******:****  :*  :   ***:*:***: ******::*** *::******
cow*   CSASVCQPAGTPSCVTLCP-ARRRRSSDIHFQNNTASISSKGPLILLQAIQDSSEKLHKY
pig*   CTASVCKPAGAPICVTTCPAARRRRSSDIHFQNGTASISSKGPMILLQATRDSSERLHKY
cat*   CNVSICQPAGTSSCRITCPVARRRRHSDLHHHSSTASISSKGPMILLQATMDSAEKLHKN
       *..*:*:*** .  *  *|**:*.:..**********:***** *:*:***
cow*   SRSPVDSQALWVAGLSGILIVGALFMSYLAIRKWR
pig*   SRPPVDSHALWVAGLLGSLIIGALLVSYLVFRKWR
cat*   SSSPIDSQALWMAGLSGTLIFGFLLVSYLAIRKRR
       * .*:**:***:***  * **.* *::***.:** *
```

FIG. 4

Cat/pig

```
Score = 146 bits (368), Expect = 1e-34
 Identities = 80/162 (49%), Positives = 95/162 (58%), Gaps = 40/162 (24%)

Cat:   71  GCGTWVRESPGGSVLLDASYSSCYVNEWVSTTQSPGTSRPPTPASRVTPQDSHYVMIVGV  130  cat
           ||||||  +  ||  |+ ++|||   |||  ||                    ||||+|  +|+    consensus
Pig:   73  GCGTWVHKGPGSSMGVEASYRGCYVTEW--------------------DSHYLMPIGL  110  pig Cat:  131  EGTDAAGRR-VTNTKVLRCPRNPPDQALVSSLSPSPLQNVALEAPNADLCDSVPKWDRLP  189
           |  ||  |  ||  ||+ +|                |+  +||+  |   |||+|| |||||
Pig:  111  EEADAGGHRTVTETKLFKC---------------PVDFLALDVPTIGLCDAVPVWDRLP  154

Cat:  190  CASSPITQGDCNKLGCCYKS-EANSCYYGNTVTSRCTQDGHF  230
           ||  |||||+|  +|||||  |   ||||||||||||||||||||||
Pig:  155  CAPPPITQGECKQLGCCYNSEEVPSCYYGNTVTSRCTQDGHF  196
```

Ferret/pig

```
Score = 162 bits (409), Expect = 1e-39
 Identities = 79/137 (57%), Positives = 90/137 (65%), Gaps = 1/137 (0%)
 Frame = +2

Ferret:10   PGSSMVLEASYSGCYVTEWVRTTQSPQMLRTPAPPSGVTPQDPHYIMLLGVEGADVTGRS  69   ferret
            |||||  +||||  |||||||||                              ||  ||+|  +|+|  ||     consensus
Pig:   82   PGSSMGVEASYRGCYVTEW--------------------DSHYLMPIGLEEADAGGHR  119  pig Ferret:70   TVTKTKLLKCPVDPPALDAPNADLCDSVPXWDRLPCAPSSISQRDCEKVGCCYNL-EANS  128
            |||+|||  |||||   |||  |     |||+|| ||||||||  |+|  +|+++||||| |     |
Pig:  120   TVTETKLFKCPVDFLALDVPTIGLCDAVPVWDRLPCAPPPITQGECKQLGCCYNSEEVPS  179

Ferret:129  CYYGNTVTSHCTQDGHF  145
            |||||||||| ||||||'||
Pig:  180   CYYGNTVTSRCTQDGHF  196
```

Ferret/cat

```
Score = 204 bits (520), Expect = 1e-52
 Identities = 97/142 (63%), Positives = 109/142 (70%), Gaps = 16/142 (10%)
 Frame = +2

Ferret:10   PGSSMVLEASYSGCYVTEWVRTTQSPQMLRTPAPPSGVTPQDPHYIMLLGVEGADVTGRS  69   ferret
            ||  |++|+||||  ||| ||| |||||       |  |  | |||| ||+|+++|||| |   ||     consensus
Cat:   80   PGGSVLLDASYSSCYVNEWVSTTQSPGTSRPPTPASRVTPQDSHYVMIVGVEGTDAAGRR  139  cat Ferret:70   TVTKTKLLKCPVDPP---------------ALDAPNADLCDSVPXWDRLPCAPSSISQR  128
            ||  ||+|+|| +||                ||+||||||||||| ||||||||  | |+|
Cat:  140   -VTNTKVLRCPRNPPDQALVSSLSPSPLQNVALEAPNADLCDSVPKWDRLPCASSPITQG  198

Ferret:129  DCEKVGCCYNLEANSCYYGNTVTSHCTQDGHF  145
            || |+|||  ||||||||||||||| |||||||
Cat:  199   DCNKLGCCYKSEANSCYYGNTVTSRCTQDGHF  230
```

FIG. 5a

Dog/Cat

```
Score = 134 bits (337), Expect = 2e-31
 Identities = 64/85 (75%), Positives = 68/85 (79%)

Dog:   1   LRCPRNPPDPTLLSSLSYSPDQNRALDVPNADLCDFVPVWDRLPCVPSPITEEDCKKIGC  60    dog
           |||||||||  |+||||  ||  ||  ||+ ||||||| || ||||||  ||||+ || |+||    consensus
Cat: 146   LRCPRNPPDQALVSSLSPSPLQNVALEAPNADLCDSVPKWDRLPCASSPITQGDCNKLGC 205    cat Dog:  61   CYNLEVNFCYYGNTVTSHCTQDGHF  85
           ||  |  | |||||||||| |||||||
Cat: 206   CYKSEANSCYYGNTVTSRCTQDGHF 230
```

FIG. 5b

CLUSTAL W (1.82) multiple sequence alignment of dog, ferret, and
cat ZPB nucleotide sequences

```
dog     ------------------------------------------------------------
ferret  ------------------------------------------------------------
cat     CAAGTACAGGTCTTGCAGCCAGTGGGGCTCCCGATGGCATCATGTGGCTGCTGCAGCCCC   60 dog     ------------------------------------------------------------
ferret  ------------------------------------------------------------
cat     TCTTGCTCTGTGTTCCCTTGTCTCTCGCTGTGCATGGCCAGCAGAAGCCCCAGGTACCAG  120 dog     ------------------------------------------------------------
ferret  ------------------------------------------------------------
cat     ATTATCCCGGTGAACTCCATTGTGGGCTCCAGAGCCTTCAGTTTGCCATAAACCCGAGCC  180 dog     ------------------------------------------------------------
ferret  ------------------------------------------------------------
cat     CCGGGAAAGCGACTCCTGCACTCATAGTCTGGGACAATCGCGGGCTGCCACACAAGCTGC  240 dog     ---------------------------GAGGGCCCAGGAAGCTCCATGGTGTTAG   28
ferret  ---------------------------GAAGGCCCAGGCAGCTCCATGGTGCTAG   28
cat     AGAACAACTCTGGCTGCGGTACCTGGGTAAGGGAGAGCCCGGGGGCTCCGTGCTGTTAG  300
                                            * dog     AAGCCCTCTTATGATGGCTGCTATGTCACCGAGTGGGTGAGGACGACTCGATCACCAGAAA   88
ferret  AAGCCCTCTTACAGCGGCTGCTATGTCACCGAGTGGGTAAGGACCACCACCATCGCCACAA   88
cat     ACGCCCTCTTACAGCAGCTGCTATGTCAACGAGTGGGTGAGCACGACCCAATCCCCAGGAA  360
        * ********* *  ********** ******* **  *  *  *** **
```

FIG. 8

```
dog     TGCCGAGACCCCGTGTGTCACCATCAGGGGTGTCTCCCCAGGACCCCACTATGTCATGC  148
ferret  TGCTGCGAACCCCTGCACCACCACCATCAGGGGTGACTCCCCAGGATCCCCACTATCATGC 148
cat     CGTCGAGGCCCCCCCACCCCAGCATCCAGGGTGACTCCCCAGGACTCCCACTACGTCATGA 420
                * * *     **  **  * *** *  * ** ** * dog     TGGTTGGAGTTGAAGGAGCAGATGTGGCTGGACGCAACATGTTACAAAGACACAGCTGC   208
ferret  TACTTGGAGTTGAAGGAGGAGCAGATGTGACTGGACGCAGATGTTACAAAGACAGAAGCTGC 208
cat     TAGTCGGAGTTGAAGGCACAGATGCGGGCTGGGGCCAG---GGTTACCAACACCAAGGTGC 477
        *  * **********  **** * * ***  * *    *   ** dog     TCAGGTGTCCTATGGATCCCCCAGACCCAACTTTGTTATCTAGCTTGAGTTACTCTCCTG 268
ferret  TTAAGTGTCCTGTGTGATCCCCAG---------------------------------     232
cat     TCAGGTGTCCTAGGAATCCCCAGACCAAGCTTTGGTGTCGAGCTTAAGTCCCCTCCCTC   537
        * * *******    *  ******* dog     ATCAAAACAGAGCCCTAGATGTTCCAAATGCTGATCTGTGTGACTTTGTCCCAGTGTGGG 328
ferret  ---------CCCTAGATGCTCCAAACGCTGACCTGTGTGATTCTGTCCTCCAGTGTGGG   280
cat     TTCAAAACGTAGCACTAGAAGCTCCAAACGCTGACTTGTGTGACTCTGTCCCAAAGTGGG 597
                   *  **** * *  ** *** * ***** * * ***   *** dog     ACAGGCTGCCATGTGTTCCTTCACCCATCACTGAAGAGACTGCAAGAGATTGGTTGCT   388
ferret  ACAGGCTGCCATGTCTGCTCCTTCATCTATCAGTGAAAGAGATTGTGAGAAGGTTGGTTGCT 340
cat     ACAGGCTTCCGTGTGTTCCTTCTTCACCCATCAGGGAGACTCAGGGGAACTAAGCTTGGTTGCT 657
        *****  *    * *   *    * *  *    **    * *** dog     GCTACAATTTGGAGGTGAATTTCTGTTATTATGGAAAACACAGTGACCTCCCACTGTACCC   448
ferret  GCTACAATTTGGAGGCTAATTCCTGTACTACTATGGAAAACACAGTGACGTCCCACTGTACCC 400
cat     GCTACAAATCAGGAGGCAAATTCCTGTTACTACTATGGAAAACACAGTGACCAGCTCACGCTGTACCC 717
        *******       * * **** * **  *  ******************* **   ******
```

FIG. 8
(CONTINUED)

```
dog     AAGATGGCTACTTCTACATCGCTGTGTCTCGGAATGTGACCTCACCCCCACTTCTCTTGA  508
ferret  AAGATGGCCACTTCTCCACTTGTCGTGTCTCGGAAGGTGACCTCACCCCCACTGCTCTTAA 460
cat     AAGACGGCCACTTCTCCATCGCCGTGTCTCGGAACGTGACCTCACCCCCACTGCTCTTAA  777
        ** * **** * * **************  ********* *** dog     ATTCTGTGCGCTTGGCCTTCAGGAATGATGTGGAATGTACCCCTGTGATGGCAACACACA  568
ferret  ATTCTGTGCGCTTGGCCTTCAGGAATGATGACCATGAATGACCACCCTGTGATGACACACACA 520
cat     ATTCTCTGCGCTTGGCCTTCGGGAAGGACCGCGAATGTAACCCTGTGAAAGCAACACGTG  837
        *** ************ * ****   *   **   ****    *** dog     CTTTTGCCCTATTCTGGTTTCCATTTAACTCCCTGTGGTACCACAAGACGGATCACTGGAG  628
ferret  CCTTTGCCACCTTTGGTTTCCATTAAATTCCTGTGGTACCACAAGACGGATCATTGGAG  580
cat     CCTTTGCCCTGTTCTTTTTCCATTTAATTCCTGTGGCACCACGAGATGGGTCACTGGAG  897
        * ****** * ***  *  *****  *******  *  *  * ***** dog     ACCAGGCAGTATATGAAAATGAGCTGGTTGCAGCTAGAGATGTTAGAACTTGGAGCCATG  688
ferret  ACTGGGTAGTATATGAAAATGAGCTGGTCGTCGCAACTAGAGATGTGAGAGCTTGGAGCCATG 640
cat     ACCAGGCAGTATATGAAAATGAGCTGGTGGCAGCTAGAGATGTGAGAACTTGGAGCCATG  957
          *******************   * * ******* * ********** dog     GTTCTATCACCCGTGACAGTATTTCAGGCTCCGAGTTAGCTGCAGCTACTCTATAAGTA  748
ferret  GTTCTATCACCCGTGACAGTATTTCAGGCTTCAAGTTAGCTGCAGCTACTACTGATCAGCA  700
cat     GTTCTATTACCCGTGACAGTATCTTCAGGCTTCGAGTTAGCTGCAGCTACTCTGTAAGGA 1017
        ***** ********** *****  * **************** *  *  * dog     GCAATGCCTTCCCAGTTAATGTCCACGTGTTTACATTTCCACCACCGCCATTCTGAGACCC  808
ferret  GCAATGCCTCCCCAGTTAGTGTCTAATGCCTCCCACCACCCCTTCCTGAAACCC  760
cat     GTAATGCCTTCCCGGCTTAGCGTTCAGGTGTTTACCATCCCACCACCCATCCCATCTGAAAACCC 1077
        * ******* *** ** *     *  * * *       *    *  ***  *  * ****
```

FIG. 8
(CONTINUED)

```
dog      AGCCTGGACCCCTCACTCTGGAACTCAAGATTGCCAAGGATAAGCACTATGGTTCCTACT  868
ferret   AGGCTGGACCCCTTACTCTGGAACTCAAGATTGCCAAGATAAGCACTATGAATCCTATT   820
cat      AGCATGGACCCCTCACTCTGGAACTCTGGAACTCAAGATTGCCAAAGATAAGCACTATGGCTCCTACT 1137
           ***** ***************** *****  *** ***** dog      ACACTGCTGGTGACTACCCAGTGGTGAAGCTACTTCGGGATCCCATTTATGTGGAGGTCT  928
ferret   ACACTGCCAGTGACTACCCAGTGGTGAAGCTGTTGAAGCTGTCTTCGGGATCCCATTTACGTGGAGGTGT  880
cat      ACACTATTGGTGACTACCCAGTGGTAAAGTTGCTTCGGGATCCCATTTATGTGAGGTCT  1197
         ***   ********* * *  *********  * ********* dog      CTATCCGCCACAGAACAGACCCCCACCTGGGGCTGCTCCTCCATTACTGTTGGGCCACAC  988
ferret   CTATCCGCCACAGAACAGACCCCCTACCTGGGGCTGTTCCTCCAGCACTGTGTGGGCCACAC  940
cat      CTATCCGCCACAGAACGGACCCCCTCCCTGGGGCTGCTCCTGCTCCATAACTGTTGGGCCACAC 1257
         ************** **    **** *   *     ************ dog      CCAGCAGAAACCCACAGCATCAGCCCCAGTGGCTCATGCTGGTGAAAGGCTGCCCCTA--  1046
ferret   CCAGCCTAAACCCCAACATCAGGCCAGGCCATGCCAGTGGCTGGTCAATGGCTGCCCTTA-- 998
cat      CCGGCAAGAACTCCCAGAGTCTGTCCCAGAGTCTGTCCCAGTGGCCCATTCTGTGAAAGGATGCCCTACG 1317
             **    *   *    **    *     ***   *  **   * dog      ------------------------------------------------------------
ferret   ------------------------------------------------------------
cat      TTGGAGACAACTATCAAACCCAGCTGATCCCTGTCCAGAAGGCTCTGGATACACCATTTC 1377 dog      ------------------------------------------------------------
ferret   ------------------------------------------------------------
cat      CATCTTACTACAAGCGCTTCAGTATTTCACCTTTGTGGACACCATGGCAAAGT        1437
```

FIG. 8
(CONTINUED)

```
dog      ------------------------------------------------------------
ferret   ------------------------------------------------------------
cat      GGGCACTCAGGGGACCGGTGTATCTGCACTGTAATGTATCCATCTGCCAGCCTGCTGGGA 1497 dog      ------------------------------------------------------------
ferret   ------------------------------------------------------------
cat      CCTCCTCCTGTAGGATAACCTGTCCTGTTGCCAGGCGAAGAAGACACTCTGACCTCCATC 1557 dog      ------------------------------------------------------------
ferret   ------------------------------------------------------------
cat      ATCACAGCAGTACTGCGAGCATCTCTAGCAAGGGTCCCATGATTCTACTCCAAGCCACTA 1617 dog      ------------------------------------------------------------
ferret   ------------------------------------------------------------
cat      TGGACTCTGCAGAGAAGCTCCACAAAAACTCAAGTTCTCCTATAGACTCCCAAGCTCTGT 1677 dog      ------------------------------------------------------------
ferret   ------------------------------------------------------------
cat      GGATGGCAGGCCTTTCCGGGACCCTAATCTTTGGATTCTTGTTAGTGTCCTACTTGGCTA 1737 dog      ------------------------------------------------------------
ferret   ------------------------------------------------------------
cat      TCAGGAAACGGAGGTGAATTATTCCAGTTGTGTTAATAAAACCAGATTGCATTACC 1793
```

FIG. 8
(CONTINUED)

CLUSTAL W (1.82) multiple sequence alignment of dog,
ferret and cat ZPB amino acid sequence

```
dog      ------------------------------------------------------------
ferret   ------------------------------------------------------------
cat      MWLLQPLLLCVPLSLAVHGQQKPQVPDYPGELHCGLQSLQFAINPSPGKATPALIVWDNR  60 dog      ------------EGPGSSMVLEASYDGCYVTEWVRTTRSPEMPRPRVSPSGVSPQ  43
ferret   ------------EGPGSSMVLEASYSGCYVTEWVRTTQSPQMLRTPAPPSGVTPQ  43
cat      GLPHKLQNNSGCGTWVRESPGGSVLLDASYSSCYVNEWSTTQSPGTSRPPTPASRVTPQ  120
                     *.*:  ;*:* ..* . ;*   . .:  * ..*** dog      DPHYVMLVGVEGADVAGRNMVTKTQLLRCPMDPPDPTLLSSLSYSPDQNRALDVPNADLC  103
ferret   DPHYIMLLGVEGADVTGRSTVTKTKLLKCPVDPP------------ALDAPNADLC  87
cat      DSHYVMIVGVEGTDAAGR-RVTNTKVLRCPRNPPDQALVSSLSPSPLQNVALEAPNADLC  179
         * *:: ****   .*:  .  ** *:  **  .*     .   :     ****** dog      DFVPVWDRLPCVPSPITEEDCKKIGCCYNLEVNFCYYGNTVTSHCTQDGYFYIAVSRNVT  163
ferret   DSVPVWDRLPCAPSSISQRDCEKVGCCYNLEANSCYYGNTVTSHCTQDGHFSIVVSRKVT  147
cat      DSVPKWDRLPCASSPITQGDCNKLGCCYKSEANSCYYGNTVTSRCTQDGHFSIAVSRNVT  239
         * ** ******. *.*: *  **:: ****:   . *******;*:*****:* :*:**

dog      SPPLLLNSVRLAFRNDVECTPVMATHTFALFWFPFNSCGTTRRITGDQAVYENELVAARD  223
ferret   SPPLLLNSVRLAFRNDHECTPVMTTHTFATFWFPLNSCGTTRRIIGDWVVYENELVATRD  207
cat      SPPLLNSLRLAFGKDRECNPVKATRAFALFFFPFNSCGTTRWVTGDQAVYENELVAARD  299
         ****  *;****   :* *   :;::*:***      ;*******;:* dog      VRTWSHGSITRDSIFRLRVSCSYSISSNAFPVNVHVFTFPPPHSETQPGPLTLELKIAKD  283
ferret   VRAWSHGSITRDSIFRLQVSCSYLISSNASQVNVQIFTLPPPLPETQAGPLTLELKIAKD  267
cat      VRTWSHGSITRDSIFRLRVSCSYSVRSNAFPLSVQVFTIPPPHLKTQHGPLTLELKIAKD  359
         **:************;***** ; **.  *;:*: ***;***    ** **********
```

FIG. 9

```
dog     KHYGSYYTAGDYPVVKLLRDPIYVEVSIRHRTDPHLGLLLHYCWATPSRNPQHQPQWLML 343
ferret  KHYESYYTASDYPVVKLLRDPIYVEVSIRHRTDPYLGLFLQHCWATPSLNPQHQRQWPML 327
cat     KHYGSYYTIGDYPVVKLLRDPIYVEVSIRHRTDPSLGLLLHNCWATPGKNSQSLSQWPIL 419
        *    ***********************.  .:  ******  *.:* dog     VKGCP------------------------------------------------------ 348
ferret  VNGCP------------------------------------------------------ 332
cat     VKGCPYVGDNYQTQLIPVQKALDTPFPSYKRFSIFTESFVDTMAKWALRGPVYLHCNVS  479
        *:*** dog     ----------------------------------------------------------- 
ferret  ----------------------------------------------------------- 
cat     ICQPAGTSSCRITCPVARRRRHSDLHHHSSTASISSKGPMILLQATMDSAEKLHKNSSSP 539 dog     ---------------------------------
ferret  ---------------------------------
cat     IDSQALWMAGLSGTLIFGELLVSYLAIRKRR   570
```

FIG. 9
(CONTINUED)

ANTIGENS FOR IMMUNOCONTRACEPTION

CROSS REFERENCE TO RELATED APPLICATIONS

This application claims the benefit of U.S. 60/354,525 filed Feb. 8, 2002 and U.S. 60/380,293 filed May 15, 2002, and is a continuation in part of PCT/CA03/00177 filed Feb. 10, 2003, the contents of all of which are herein incorporated by reference.

FIELD OF THE INVENTION

The present invention relates to the field of immunology, in particular, to immunocontraceptive vaccines.

BACKGROUND OF THE INVENTION

Increasing populations of feral or stray domestic dogs and cats has been a growing problem in North America and the rest of the world. For example, an estimated 40% of domestic cats (Felis catus) in the United States are classified as feral or stray.

Concerns about impacts on wildlife, transmission of infectious diseases, and the welfare of the cats and dogs themselves have led to various strategies to reduce the number of feral cats and dogs. Locally, and throughout the world, extermination has been the dominant method used in the attempt to control free-ranging feral cats and dogs.

Surgical sterilisation of feral cats and dogs by veterinarians followed by release back into the colony has been increasingly utilised as a humane tool to lower feral cat and dog populations in the last 2 decades. Despite the success of large-scale surgical sterilisation, such programs are not financially or logistically feasible in many locations.

During the last decade, interest has increased in applying immunocontraception (IC) as a reliable method to lower population of pest species. IC can be a humane means of reducing fertility in domestic, feral and wild mammals (Oogjes, 1997), and several potential IC targets exist. For example, a vaccine that used gonadotrophin-releasing hormone (GnRH) as antigen, depressed ovarian activity in horses for one breeding season (Bradley et al., 1999). The difficulty with GnRH directed vaccines is that there is a potential for endocrine dysfunction (Muller et al., 1997).

Zona pellucida (ZP), a noncellular glycoprotein coat surrounding the mammalian egg, regulates sperm-egg interaction during fertilisation (Sacco and Yurewicz, 1989). This structure is an ideal candidate for a contraceptive target, since altering its structure can prevent pregnancy. ZP immunisation has been effective in lowering fertilization rates of many mammals (Willis et al., 1994; Kirkpatrick et al., 1996; Brown et al., 1997a,b; Harris et al., 2000). Two independent reports have indicated that pig *zona pellucida* (pZP) is an effective immunocontraceptive (although requires multiple boosters) in domestic cats (Ivanova et al., 1995; Bradley et al., 1999). Porcine zona pellucida has also been used in liposome-based immunocontraceptive vaccines for reducing fertility of certain mammals by 90–100% with a multi-year efficacy (Brown et al., 2001). However, use of pZP in such a liposome-based vaccine as a single administration vaccine for cats is ineffective in cats (Gorman et al., 2002).

SUMMARY OF THE INVENTION

There is described an immunocontraceptive vaccine for cats and/or dogs comprising a zona pellucida polypeptide, and/or a variant thereof, from a carnivorous mammal and a physiologically acceptable auxiliary.

There is further described a method for reducing fertility in cats and/or dogs comprising administering to a cat or a dog an immunocontraceptive vaccine comprising a zona pellucida polypeptide, and/or a variant thereof, from a carnivorous mammal and a physiologically acceptable auxiliary.

There is still further described the use of a zona pellucida polypeptide, and/or a variant thereof, from a carnivorous mammal for reducing fertility in cats and/or dogs or for preparing a medicament for reducing fertility in cats and/or dogs.

There is yet further described a commercial package comprising a zona pellucida. polypeptide, and/or a variant thereof, from a carnivorous mammal together with instructions for its use in reducing fertility in cats and/or dogs.

There is still yet further described an isolated DNA molecule that codes for a zona pellucida polypeptide, and/or a variant or hybrid thereof, from ferret and/or dog.

There is also described a zona pellucida polypeptide, or a variant thereof, from a ferret (SEQ ID NOS: 2, 6 and 12).

There is also described an isolated polypeptide comprising a sequence selected from the group consisting of: (a) SEQ ID NO: 16; (b) SEQ ID NO: 14; (c) SEQ ID NO: 8; (d) SEQ ID NO: 6; (e) SEQ ID NO: 4; (f) SEQ ID NO: 2; (g) an amino acid sequence which is substantially identical to any one of (a) to (f); and (h) an immunologically active fragment of at least 12 amino acids in length of any one of (a) to (g).

There is also described a composition comprising the polypeptide described above and a carrier or diluent suitable for use in a vaccine.

There is also described an isolated DNA encoding the polypeptide described above and an expression vector comprising such DNA and a host or host cell comprising such expression vector.

There is also described a kit for inducing infertility in a mammal comprising the polypeptide described above and instructions for its use in eliciting an immune response against native zona pellucida in a mammal.

There is also described a method for inducing anti-ZPB antibodies in a mammal, the method comprising administering to the mammal at least one polypeptide described above, wherein said administering induces production of an antibody that binds mammalian zona pellucida.

There is also described a method for inducing infertility in a mammal comprising administering to the mammal at least one polypeptide described above.

There is also described a method of inducing infertility in a mammal comprising administering at least one polypeptide described above, wherein said administering induces production of an antibody that binds mammalian zona pellucida.

There is also described a method of producing the polypeptide described above comprising culturing the host or host cell described above.

There is also described an antibody immunoreactive to the polypeptide described above.

There is also described an antibody as described above which is immunoreactive against native zona pellucida from at least 2 sources.

BRIEF DESCRIPTION OF THE DRAWINGS

The invention will now be described by way of example having regard to the appended drawings.

FIG. 4 shows an alignment of mammalian zona pellucida sequences from cow (SEQ ID NO: 9), pig (SEQ ID NO: 10) and cat (SEQ ID NO:11).

FIG. 5 shows alignments of specific zona pellucida sequences between various species:

Cat/pig: amino acids 71–230 of cat SEQ ID NO:11 aligned with amino acids 73–196 of pig SEQ ID NO:10;

Ferret/pig: amino acids 10–145 of ferret SEQ ID NO:6 aligned with amino acids 82–196 of pig SEQ ID NO:10;

Ferret/cat: amino acid 10–145 of ferret SEQ ID NO:6 aligned with amino acids 80–230 of cat SEQ ID NO:11; and Dog/cat: amino acids 1–85 of dog SEQ ID NO:8 aligned with amino acids 146–230 of cat SEQ ID NO:11.

Figure 6:
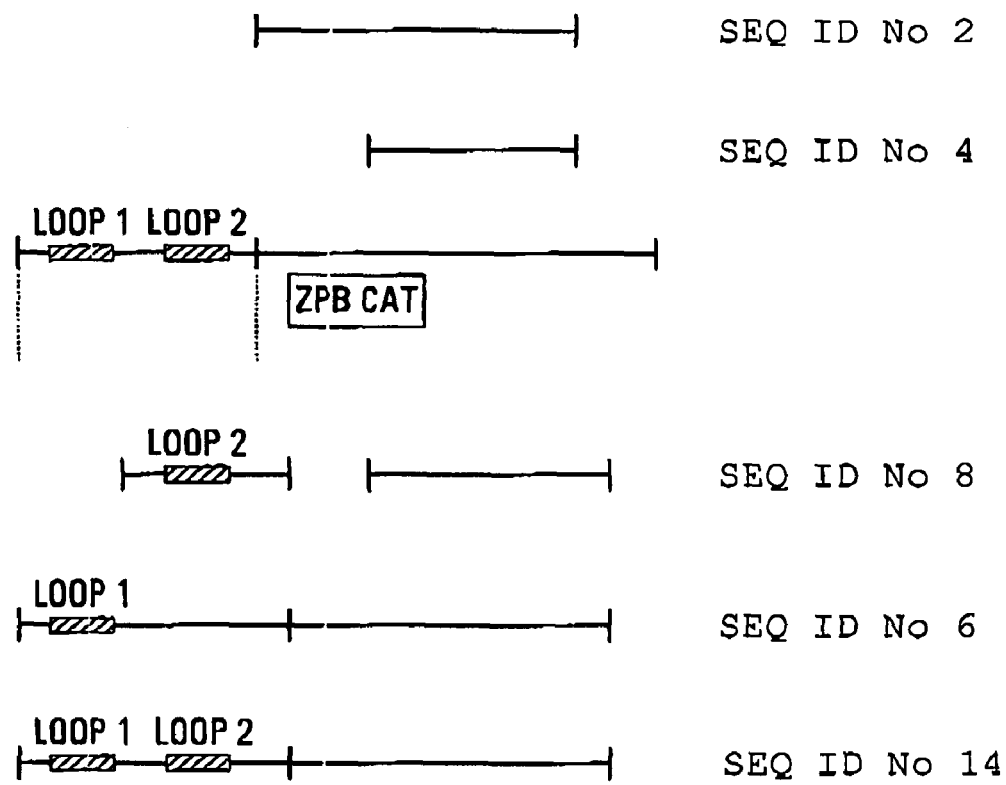

FIG. 6 is a schematic depiction of the alignment of the zona pellucida sequences.

Figure 7:
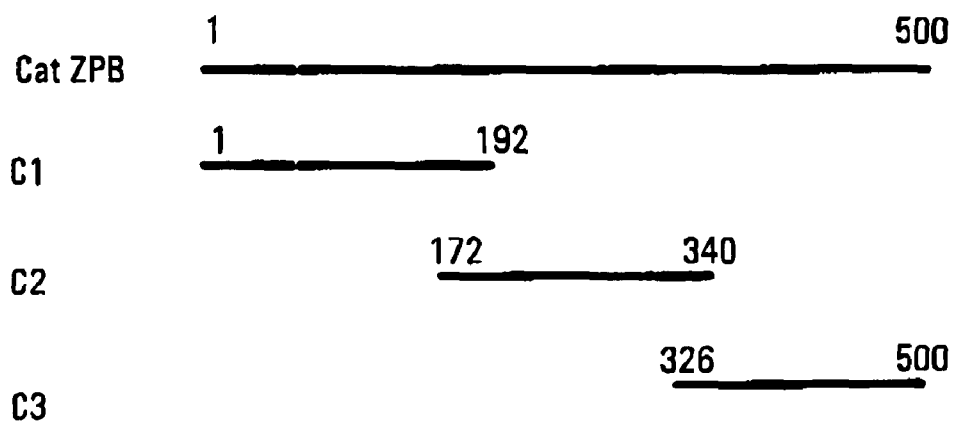

FIG. 7 is a schematic depiction of clones C1, C2, and C3 spanning cat ZPB (amino acids 1–500).

FIG. 8 shows an alignment of nucleotide sequences encoding mammalian zona pellucida for dog (SEQ ID NO:13), cat (SEQ ID NO:17) and ferret (nucleotides 22–1019 of SEQ ID NO:5).

FIG. 9 shows an alignment of mammalian zona pellucida sequences for dog (SEQ ID NO:14), cat (SEQ ID NO:11) and ferret (amino acids 8–339 of SEQ ID NO:6).

DETAILED DESCRIPTION OF THE PREFERRED EMBODIMENTS

The invention described herein pertains to immunocontraception of mammals, in particular, cats and dogs. The target is the outermost covering of the mammalian egg (oocyte) called the zona pellucida. Cat and dog zona pellucida (ZP) consists of three components namely ZPA, ZPB and ZPC. Cat ZP is poorly immunogenic in cats and dog ZP is poorly immunogenic in dogs. To achieve immunocontraception using ZP as antigen, one must have a ZP which is foreign enough to provoke a good immunogenic reaction while at the same time similar enough that antibodies against the candidate ZP cross-react well with the target. In one embodiment of this disclosure, a fused protein consisting of hitherto unknown ferret and dog ZPB protein sequences is shown to be immunogenic in several mammalian species, in particular, cats. Antibodies raised against the fused ferret/dog sequence also block sperm binding to oocytes of dog or any other mammal whose ZPB contains an amino acid sequence which is similar to the targeted cat ZPB sequence. Antibodies raised against the amino acid sequences described herein lessen fertilization in mammals such as cats and dogs. A description of the corresponding cat ZPB segments is included for comparative purposes, however for a further description of cat ZPB sequences, see Harris et al., 2000, as well as FIG. 4.

To determine the region of cat ZPB responsible for sperm binding, three recombinant polypeptides derived from cat ZPB that spanned the length of cat ZPB protein were produced in *Escherichia coli* then injected into rabbits to generate antibodies against each of the three regions of cat ZPB. These antibodies were used to study in vitro fertilization of cat oocytes to determine the regions of cat ZPB responsible for sperm binding. Fused ferret/dog recombinant protein corresponding to the sperm binding site were designed, produced and injected in different mammals to confirm immunogenicity in multiple species. Cross reactivity of antibodies against the fused ferret/dog recombinant protein for the sperm binding site of cat ZPB was confirmed by ELISA. The ability of antibodies against the recombinant fused ferret/dog construct to ))lock cat sperm binding to cat oocytes was determined in vitro. The results confirm that antibodies raised against the fused ferret/dog construct reduce cat sperm binding to cat oocytes, providing evidence of reduced cat fertility, and by extension, fertility of other mammals whose ZPB contains an amino acid sequence which is similar to the targeted cat ZPB sequence.

Zona pellucida (ZP) polypeptides have now been identified that act as antigens to induce the production of antibodies with a high affinity for cat and dog zona pellucida and hence cat and dog oocytes. Since immunocontraception (IC) based on use of ZP antigens relies on a balance between antigenicity of foreign ZP and the ability of antibodies raised against the foreign ZP to bind to the ZP on the targeted oocyte surface, zona pellucida from animals more closely related to cats and/or dogs, than is the pig, could prove useful in IC of cats provided satisfactory production of antibodies is induced. It has now been found that ZP antigens from carnivorous mammals are particularly useful in preparing immunocontraceptive vaccine that are capable of producing immune responses in cats and/or dogs. ZPB is particularly useful as the antigen. In particular, the carnivorous mammals may be selected from the group consisting of cat (e.g. *Felis catus*), dog (e.g. *Canis familiaris*), ferret (e.g. *Mustela putorius furo*), and mink (e.g. *Mustela vison*). Thus, cat ZP (cZP), dog ZP (dZP), ferret ZP (feZP), mink ZP (mZP) and/or variants thereof are particularly useful as antigens in the immunocontraceptive vaccine. More particularly, cat ZPB (cZPB), dog ZPB (dZPB), ferret ZPB (feZPB), mink ZPB (mZPB) and/or variants thereof are preferred.

The term 'variants' means recombinant or denatured proteins or peptides, or fragments thereof, or fragments of native ZP, which are capable of producing the desired immune response in cats and/or dogs. Substitutions, additions and/or deletions of native or recombinant ZP are encompassed by variants. Variants are generally at least 50% homologous to native ZP. Variants having homology of at least 55%, 60%, 65%, 70%, 75%, 80%, 85%, 90% or 95% to the native ZP are also particularly contemplated within the scope of the invention. Fragments of native, recombinant or denatured ZP proteins or peptides are generally at least 12, 14, 16, 18, 20, 22, 24, 26, 28, 30, 32, 34, 36, 38, 40, 44, 46, 48 or 50 amino acids in length. Preferably, such fragments include amino acids VSTTQSPGTSRPPTPASRVTPQ (amino acid numbers 29 to 50 of cat zona pellucida), (amino acids 99 to 120 of SEQ ID NO:11), and PRNPPDQALVSSLSPS (amino acid numbers 79 to 94 of cat zona pellucida), amino acids 149 to 164 of SEQ ID NO:11, and VRTTQSPQMLRTPAPPSGVTPQ (from SEQ ID NO 6), and PTLLSSLSYSPDQNR (from SEQ ID NO 8).

The polyoeotides of the invention include any combination of the above fragments and their consensus sequences.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, erg., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The present invention includes amino acid sequences which are homologous to SEQ ID NOS: 2, 4, 6, 8, 14 and 16, and the fragments above. As used herein, "homologous amino acid sequence" is any polypeptide which is encoded, in whole or in part, by a nucleic acid sequence which hybridizes at 25–35° C. below critical melting temperature (Tm), to any portion of the nucleic acid sequence of SEQ ID NOS: 1, 3, 5, 7, 13 and 15. A homologous amino acid sequence may be one chat differs from an amino acid sequence shown in SEQ ID NOS: 2, 4, 6, 8, 14 or 16 by one or more conservative amino acid substitutions.

Homologous amino acid sequences include sequences that are identical or substantially identical to SEQ ID NOS: 2, 4, 6, 8, 14 or 16. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 50%, 55%, 60%, 65%, 70%, 75%, 80%, and even more preferably 85%, 87%, 90%, 93%, 96% and most preferably 99% identical to SEQ ID NOS:1, 3, 5, 7, 13 or 15.

As used herein, a fusion polypeptide is one that contains a polypeptide or a polypeptide derivative of the invention fused at the N- or C-terminal end to any other polypeptide. A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the. peptide tail is already present. These and ocher expression systems provide convenient means for further purification of polypeptides and derivatives of the invention. Alternatively, various fragments of the polypeptides of the invention may be fused together to produce chimeric polypeptides.

Accordingly, another aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

Antigens of the present invention may be formulated into vaccines in a number of ways. Methods of formulating vaccines in general are well known to those skilled in the art (for example, see Harlow et: al., 1988). Ivanova et al., 1995; Bradley et al., 1999; and Brown et al., 2001, specifically disclose methods of formulating ZP antigens into a vaccine. Immunocontraceptive vaccines comprising the ZP antigens of the present invention may be formulated as either single or multiple administration vaccines. Single administration vaccines using a system such as that described in Brown et al., 2001 are preferred.

The amount of ZP antigen used in a dose of the immunocontraceptive vaccine can vary depending on the source of the antigen and the size of the cat or dog or other mammal. One skilled in the art will be able to determine, without undue experimentation, the effective amount of antigen to use in a particular application. The amount typically used falls in the range from about 15 µg to about 2 mg per dose. Preferably, the range is from about 20 µg to about 2 mg per dose, more preferably from about 20 µg to about 200 µg, and even more preferably from about 40 µg to about 120 µg. Typically, the amount for a small animal is about 50 µg per dose while for a large animal it is about 100 µg per dose.

Physiologically acceptable auxiliaries for immunocontraceptive vaccines are generally known in the art. Auxiliaries include carriers, diluents, adjuvants and any other typical vaccine ingredients.

Carriers and/or diluents are generally well known in the art. Typically, aqueous solutions, aqueous emulsions of an oil such as mineral oil, and non-aqueous media such as pure mineral oil may be used as carriers and/or diluents.

Suitable adjuvants include alum, other compounds of aluminum, *Bacillus* of Calmette and Guerin (BCG), TITER-MAX, RIBI, Freund's Complete Adjuvant (FCA) and a new adjuvant disclosed by the United States Department of Agriculture's (USDA) National Wildlife Research Center on their web site and described by Fagerstone KA et al (2002) Wildlife Contraception. The Wildlife Society Technical Review 02-2. Alum, other compounds of aluminum, TITER-MAX and the new USDA adjuvant are preferred.

Alum is particularly preferred as the adjuvant. Alum is generally considered to be any salt of aluminum, in particular, the salts of inorganic acids. Hydroxide and phosphate salts are particularly useful as adjuvants. A suitable alum adjuvant is sold under the trade name, ImjectAlum™ (Pierce Chemical Company) that consists of an aqueous solution of aluminum hydroxide (45 mg/ml) and magnesium hydroxide (40 mg/ml) plus inactive stabilizers. Alum is a particularly advantageous adjuvant since it already has regulatory approval and it is widely accepted in the art.

The amount of adjuvant used depends on the amount of antigen and on the type or adjuvant. One skilled in the art can readily determine the amount of adjuvant needed in a particular application. For immunocontraception, a suitable quantity of ImjectAlum™ may range from 0.1 ml/dose of vaccine to 0.5 ml/dose.

Liposomes are another typical vaccine ingredient. The vaccines of the present invention may be formulated with or without liposomes. However, use of liposomes offers certain advantages. Liposomes are completely closed lipid bilayer membranes containing an entrapped aqueous volume. Liposomes may be unilamellar vesicles (possessing a single bilayer membrane) or multilamellar vesicles (onion-like structures characterized by multimembrane bilayers, each separated from the next by an aqueous layer. Although any liposomes may be used, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. Phospholipids that are preferably used in the preparation of liposomes are those with at least one head group selected from the group consisting of phosphoglycerol, phosphoethanolamine, phosphoserine, phosphocholine and phosphoinositol.

The amount of Lipid used to form liposomes depends on the antigen being used but is typically in a range from about 0.05 gram to about 0.5 gram per dose of vaccine. Preferably, the amount is about 0.1 gram per dose. When unesterified cholesterol is also used in liposome formulation, the cholesterol is used in an amount equivalent to about 10% of the amount of lipid. The preferred amount of cholesterol is about 0.01 gram per dose of vaccine. If a compound other than cholesterol is used to stabilize the liposomes, one skilled in the art can readily determine the amount needled in the formulation.

In one embodiment, the vaccine composition may be formulated by: encapsulating the antigen or an antigen/adjuvant complex in liposomes to form liposome-encapsulated antigen and mixing the liposome-encapsulated antigen with a carrier. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. (It should be noted that the term "liposome-encapsulated antigen" may refer to encapsulation of the antigen alone or to the encapsulation of the antigen/adjuvant complex depending on the context.) When another is used, the antigen may be first encapsulated in liposomes and the resulting liposome-encapsulated antigen is then mixed into the adjuvant in a carrier.

Liposome-encapsulated antigen may be freeze-dried before being mixed with the carrier. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant.

Formulation of the liposome-encapsulated antigen into a hydrophobic substance may also involve the use of an emulsifier to promote more even distribution of the liposomes in the carrier. Typical emulsifiers are well known in the art and include mannide oleate (ARLACEL A), lecithin, TWEEN 80, and SPAN 20, 80, 83 and 85. Mannide oleate is a preferred emulsifier. The emulsifier is used in an amount effective to promote even distribution of the liposomes. Typically, the volume ratio (v/v) of carrier to emulsifier is in the range of about 5:1 to about 15:1 with a ratio of about 10:1 being preferred.

Administration of the vaccine composition can be done by any convenient method. Vaccine compositions may be administered parenterally (including intramuscularly, subcutaneously) or rectally. Parenteral administration is preferred.

For parenteral application, particularly convenient unit dosage forms are ampoules. Techniques that deliver the vaccine by injection and by remote delivery using darts, spring loaded syringes with jab sticks, air/carbon dioxide powered rifles, Wester gun and/or Ballistivet™ biobullets and retain the biological activity are particularly preferred.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Materials and Methods

Ovaries from dogs and cats were obtained from veterinarians following spaying of pet cats and dogs. Pig, ferret, and mink ovaries were obtained from a commercial source.

Soluble isolated ZP was prepared from these ovaries as described by Brown et al. (1997b) to yield cZP, dZP, feZP, mZP, and pZP. Vaccines were constructed from the designated soluble isolated ZP (SIZP). The SIZP was encapsulated in liposomes formed using soybean L-α-lecithin (Calbiochem-Novabiochem, San Diego, Calif., USA) and cholesterol (Calbiochem-Novabiochem) in a ratio of 10:1. Single administration vaccines were formulated with 1 of 2 adjuvants, i.e. with Freund's complete adjuvant (FCA) or with alum. Rabbits were immunised with a single dose of the vaccine with FCA containing SIZP (100 µg pZP or 50 µg cZP) encapsulated in multilamellar liposomes (0.1 g lecithin and 0.01 g cholesterol) that were suspended in saline (0.25 mL) and emulsified in FCA (0.25 mL). Less cZP than pZP was used in the vaccine formulation to conserve the limited quantity of cZP available. A single dose of the vaccine with alum contained pZP (100 µg) and alum (Imject®alum, Pierce Chemical Co., Rockford, Ill., USA) encapsulated in multilamellar liposomes (0.1 g lecithin and 0.01 g cholesterol) that were suspended in saline (0.15 mL) and emulsified in mineral oil/mannide oleate (8.5:1.5, v:v, 0.25 mL). Rabbits were immunised with pZP in either vaccine with FCA or vaccine with alum or with cZP in vaccine with FCA. Serum samples were taken monthly to measure the production of anti-SIZP antibodies. Production of anti-SIZP antibodies was measured as described by Brown et al. (1997b) using protein A/alkaline phosphatase.

Gel electrophoresis and Western blotting was used to measure the affinity of anti-cZP antibodies for cZP, feZP, dZP, mZP and pZP and anti-pZP antibodies for mZP as follows. Protein samples were loaded on SDS-PAGE (12%) and analysed by Western blotting. For Western blotting, electrophoresed proteins were transferred to PVDF (Amersham) paper and blocked in QUICKBLOCKER (Chemicon). The transferred blots were probed with primary antibody at 1:500 to 1:1000 dilution of TBS-TWEEN overnight at 4° C. The blots were washed 5× with TBS-TWEEN and then incubated with peroxidase labelled secondary antibody (goat anti-rabbit Ig, Jackson, 1:8000 in TBS-TWEEN) for 30 minutes at room temperature. Blots were then washed 5X with TBS-TWEEN and signals were detected by chemiluminescence (Santa Cruz) using X-ray film.

The affinity of rabbit anti-cZP, fallow deer anti-pZP and cat anti-pZP for porcine or cat zona pellucida glycoproteins was measured by ELISA. Protein G/alkaline phosphatase (Calbiochem-Novabiochem, San Diego, Calif., USA) was used to measure fallow deer antibodies whereas protein A/alkaline phosphatase (Sigma Chemical Co.) was used to measure cat and rabbit antibodies as follows. Briefly, 1 µg of either pZP or cZP in sodium carbonate/bicarbonate buffer (100 µL, 0.035 M, pH 9.6) was pipetted into each well of a 96-well ELISA plate and allowed to incubate for 1 hour at 37° C. Unbound pZP or cZP was removed, and the wells coated with gelatin (3% gelatin in TBST buffer—Tris, 0.01 M; NaCl, 0.15 M; 0.05% TWEEN 20, pH 8.0) for 15 minutes at room temperature. The wells were then washed 5 times with TBST buffer to remove unbound gelatin. Serum samples (100 µL) were added in 2-fold dilutions using TBST from 1:50 to 1:6400 and incubated at 37° C. for 1 hour. Unbound antibody and other serum proteins were removed by washing with TBST 5 times. Bound antibody was measured with protein A or protein G/alkaline phosphatase using a DYNATECH ELISA plate reader at 405 nm. One row in each plate did not receive serum (antibody) and served as a blank. Another row in each plate received doubling dilutions of a reference rabbit anti-pZP serum. Titers were determined using the linear portion of the titration curve and all titers are expressed as a percentage of the reference serum to control for interassay variability.

Figure 1:
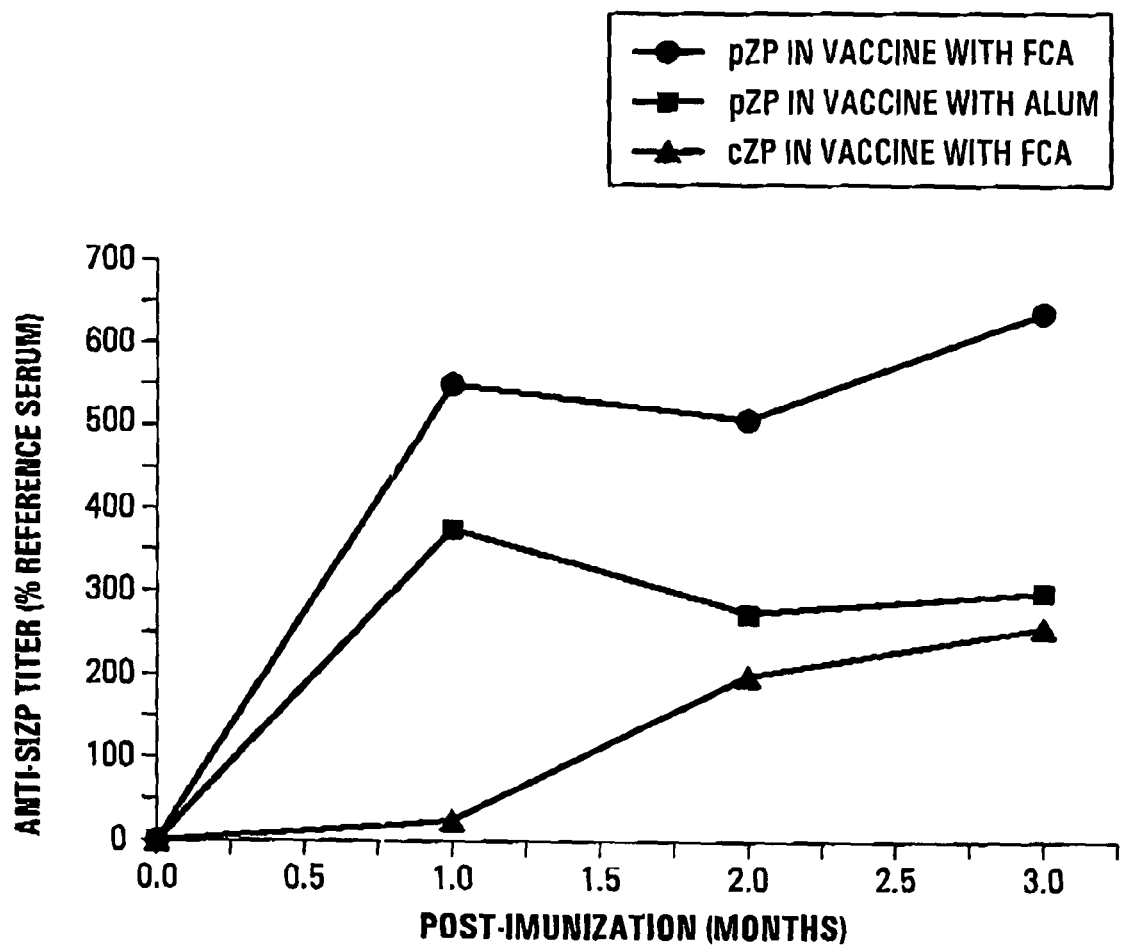
FIG. 1 is a graph showing the production of anti-SIZP antibodies by rabbits immunised with porcine zona pellucida (pZP) or cat zona pellucida (cZP) encapsulated in liposomes with either FCA or alum adjuvant as a single administration delivery system.

Results:

Native Zona Pellucida Antigens:

Rabbits immunised with pZP or cZP produced similar anti-SIZP titers 2 months post-immunisation although the anti-cZP titer was lower than the anti-pZP titers obtained with either vaccine with FCA or vaccine with alum 1 month post-immunisation (FIG. 1). This may be clue to less antigen being placed in the vaccine (½ the content of pZP). One skilled in the art can predict that production of anti-cZP antibodies will continue to increase and yield a titer similar to the anti-pZP titers. Such titers have been shown to be immunocontraceptive in a variety of mammals. Therefore, it is expected that immunisation of cats using cZP or SIZP from animals closely related to cats such as other carnivores like ferret, mink, or dog will produce anti-SIZP antibodies ill sufficient quantity to effect immunocontraception.

Figure 2:
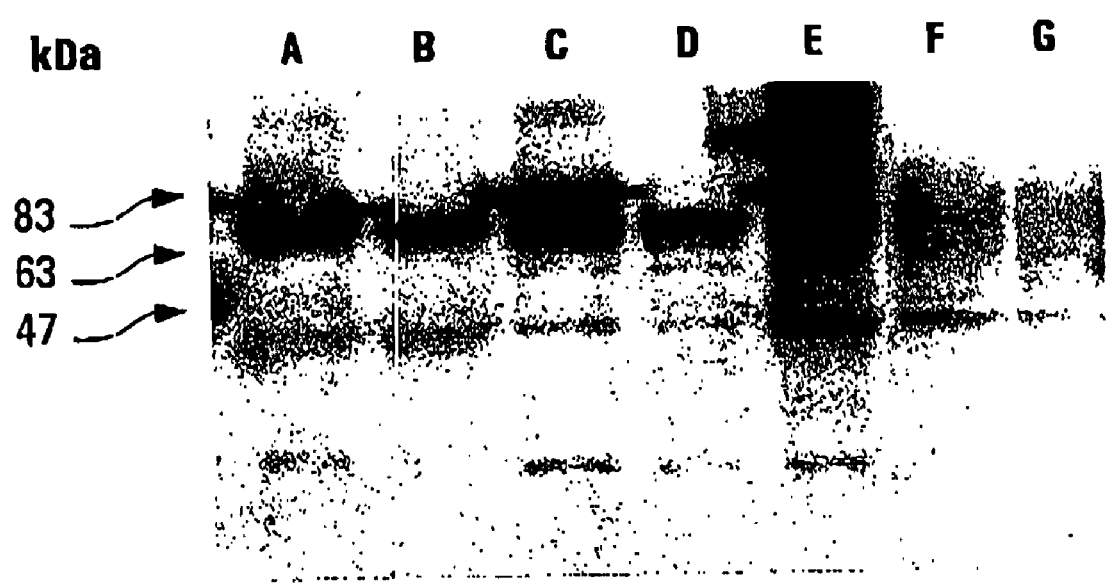
FIG. 2 is a Western blot of a gel electrophoresis of dZP (lanes A and B), feZP (lanes C and D), cZP (lane E) and pZP (lanes F and G) probed with rabbit anti-cZP antibodies showing the cross-reactivity of rabbit anti-cZP antibodies to cZP, dZP, pZP, and feZP.

Measurement of cross-reactivity of rabbit anti-cZP antibodies indicates that these antibodies cross-react strongly with dZP, feZP but there is very little cross-reactivity with pZP (FIG. 2). Zona pellucida glycoproteins (ZP glycoproteins) form bands between 63 and 83 kDa during electrophoresis. Dog, ferret, and cat ZP glycoproteins were strongly recognised by rabbit anti-cZP antibodies (see lanes A, B, C, D and E) but rabbit anti-cZP antibodies failed to recognise pZP. This result demonstrates that cZP contains more epitopes in common with dZP and feZP than with pZP and therefore there is more likelihood that antibodies raised against either dZP or feZP will cross-react with cZP and consequently bind more strongly with cat oocytes and thereby cause immunocontraception.

Figure 3:
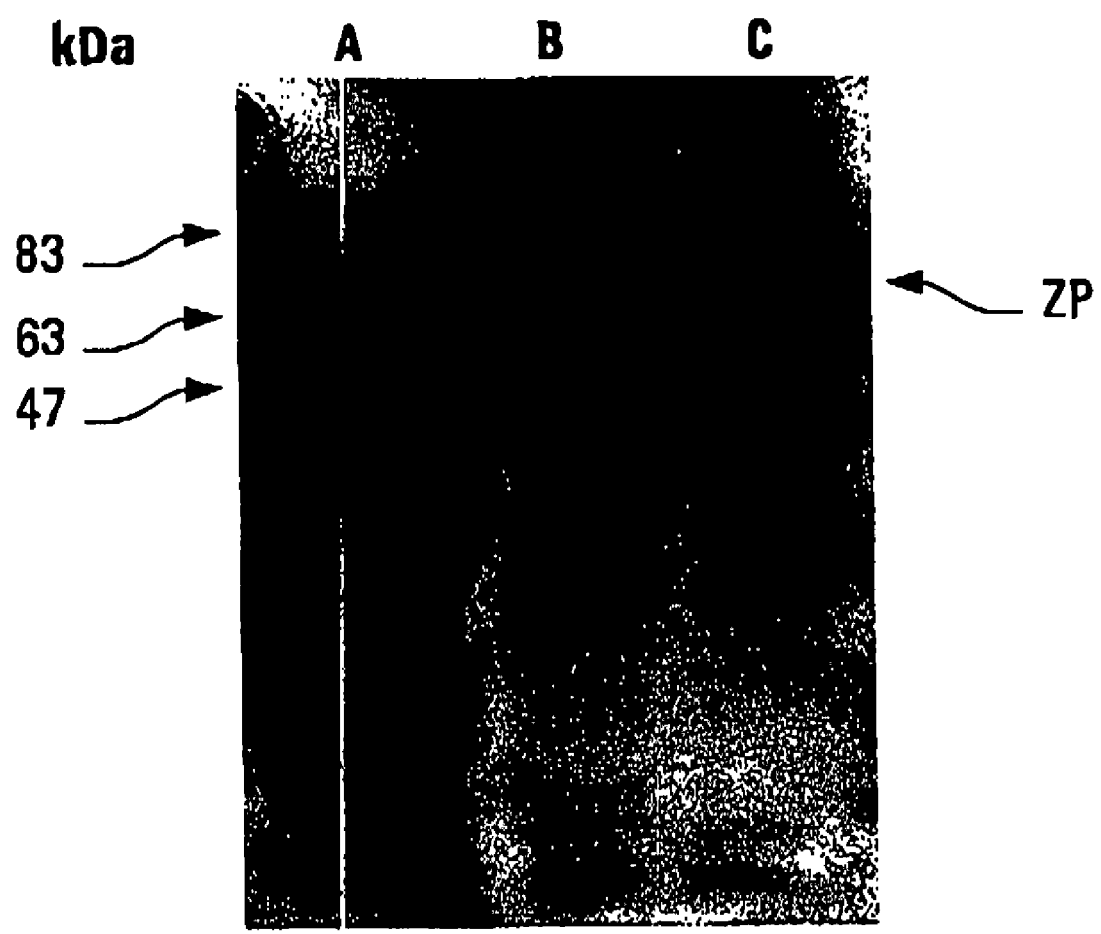
FIG. 3 is a Western blot of a gel electrophoresis of mZP (lanes A, B, and C) probed with rabbit anti-pZP antibodies (lane A) and rabbit anti-cZP antibodies (lanes B and C) showing the cross-reactivity of rabbit anti-cZP and anti-pZP antibodies to mZP.

Measurement of cross-reactivity of rabbit anti-cZP antibodies indicates that these antibodies bind more strongly with mZP than with pZP (FIG. 3). This suggests that mZP shares more epitopes with cZP than pZP and therefore one skilled in the art can predict that mZP is a good candidate antigen for the immunocontraception of cats.

Cross-reactivity can also be measured by ELISA. When titers of two cat anti-pZP sera were measured using pZP, the titers were 41% and 15% of the reference serum. However, when titers of the same antisera were measured using cZP, the titers were 2% and 2% of the reference serum. This indicates chat antibodies raised in cats against pZP have little affinity for cZP and consequently cat oocytes. When the titers of two rabbit anti-cZP sera were measured using pZP, the titers were 7% and 40% of the reference serum. However, when titers of the same antisera were measured using cZP, the titers were 32% and 200% of the reference serum. This indicates that only about 20% of antibodies raised against cZP have epitopes in common with pZP. Similarly, when titers of two fallow deer anti-pZP sera were measured using pZP the titers were 56% and 125% of the reference serum. However, when titers of the same antisera were measured using cZP, the titers were 2% and 2% of the reference serum indicating that few epitopes recognised by fallow deer immunised with pZP are found in cZP. One can conclude that the epitopes in pZP recognised by cats, rabbits and fallow deer are very different than the epitopes recognised in cZP. This :suggests that only antigens that have epitopes in common with cZP will be effective in an immunocontraceptive vaccine for cats. Based on ELISA measurements of cross-reactivity, one skilled in the art would predict that feZP, dZP, mZP or cZP would be effective antigens in an immunocontraceptive vaccine for cats.

Determination of the partial DNA sequence of feZPB allows comparison with other DNA sequences. SEQ ID NO. 1 is the partial ferret DNA sequence that codes for the equivalent of cat ZPB amino acid region 309–428. (Cat ZPB, including the leader sequence, is a total of 570 amino acids in length.)

(SEQ ID NO. 1):

gggtccgtca ctcgggacag tattttcag cttcaagtta gctgcagcta cttgatcagc agcaatgcct cccaggttaa tgtccagatt tttacgctcc caccaccct tcctgaaacc caggctggac cccttactct ggaactcaag attgccaaag ataagcacta tgaatcctat tacactgcca gtgactaccc agtggtgaag ctgcttcggg atcccattta cgtggaggtg tctatccgcc acagaacaga cccctacctg gggctgttcc tccagcactg ttgggccaca cccagcctaa accccaaca tcagcgccag tgcccatgc tggtcaatgg ctgcccttat This ferret sequence was cloned by reverse transcription/degenerate PCR method. Primers were based on multiple alignments that included ZPB sequences from cat, cow, human, possum, mouse, rat and pig ZPB. A search of GENBANK indicates that SEQ ID NO. 1 matches best with cZPB, suggesting that feZP will have many epitopes in common with cZP and therefore will be effective as an antigen in a cat immunocontraceptive vaccine.

The ferret partial amino acid sequence corresponding to the nucleotide sequence above is given by SEQ ID No. 2:

(SEQ ID NO. 2):

GSVTRDSIFR LQVSCSYLIS SNASQVNVQI FTLPPPLPET QAGPLTLELK IAKDKHYESY

YTASDYPVVK LLRDPIYVEV SIRHRTDPYL GLFLQHCWAT PSLNPQHQRQ WPMLVNGCP

SEQ ID NO. 3 is the partial nucleotide sequence of canine ZPB.

(SEQ ID NO. 3):

ggttccgtta cccgtgacag tattttcagg ctccgagtta gctgcagcta ctctataagt agcaatgcct tcccagttaa tgtccacgtg tttacatttc caccaccgca ttctgagacc cagcctggac ccctcactct ggaactcaag attgccaagg ataagcacta tggttcctac tacactgctg gtgactaccc agtggtgaag ctacttcggg atcccattta tgtggaggtc tctatccgcc acagaacaga cccccacctg gggctgctcc tccattactg ttgggccaca cccagcagaa acccacagca tcagccccag tggctcatgc tggtgaaagg ctgccccta The dog partial amino acid sequence corresponding to the nucleotide sequence above is given by SEQ ID NO. 4.

(SEQ ID NO. 4):

GSVTRDSIFR LRVSCSYSIS SNAFPVNVHV FTFPPPHSET QPGPLTLELK IAKDKHYGSY

YTAGDYPVVK LLRDPIYVEV SIRHRTDPHL GLLLHYCWAT PSRNPQHQPQ WLMLVKGCP

SEQ ID NO. 5 is another partial ferret DNA sequence that codes fox SEQ ID NO 6.

(SEQ ID NO 5):

GGCTGCGGTACCTGGGTAAGGGAAGGCCCAGGCAGCTCCATGGTGCTAGAAGCCTCTTACAGCGGC
TGCTATGTCACCGAGTGGGTAAGGACCACCCAATCGCCACAAATGCTGCGAACCCCTGCACCACCA
TCAGGGGTGACTCCCCAGGATCCCCACTATATCATGCTACTTGGAGTTGAAGGAGCAGATGTGACT
GGACGCAGCACGGTTACAAAGACAAAGCTGCTTAAGTGTCCTGTGGATCCCCCAGCCCTAGATGCT
CCAAACGCTGACCTGTGTGATTCTGTCCCAGTGTGGGACAGGCTGCCATGTGCTCCTTCATCTATC
AGTCAAAGAGATTGTGAGAAGGTTGGTTGCTGCTACAATTTGGAGGCTAATTCCTGTTACTATGGA
AACACAGTGACGTCCCACTGTACCCAAGATGGCCACTTCTCCATTGTCGTGTCTCGGAAGGTGACC
TCACCCCCACTGCTCTTAAATTCTGTGCGCTTGGCCTTCAGGAATGACCATGAATGCACCCCTGTG
ATGACAACACACACCTTTGCCACCTTTTGGTTTCCATTAAATTCCTGTGGTACCACAAGACGGATC
ATTGGAGACTGGGTAGTATATGAAAATGAGCTGGTCGCAACTAGAGATGTGAGAGCTTGGAGCCAT
GGTTCTATCACCCGTGACAGTATTTTCAGGCTTCAAGTTAGCTGCAGCTACTTGATCAGCAGCAAT
GCCTCCCAGGTTAATGTCCAGATTTTTACGCTCCCACCACCCCTTCCTGAAACCCAGGCTGGACCC
CTTACTCTGGAACTCAAGATTGCCAAAGATAAGCACTATGAATCCTATTACACTGCCAGTGACTAC
CCAGTGGTGAAGCTGCTTCGGGATCCCATTTACGTGGAGGTGTCTATCCGCCACAGAACAGACCCC
TACCTGGGGCTGTTCCTCCAGCACTGTTGGGCCACACCCAGCCTAAACCCCCAACATCAGCGCCAG
TGGCCCATGCTGGTCAATGGCTGCCCTTA (SEQ ID NO 6):

GCGTWVREGPGSSMVLEASYSGCYVTEWVRTTQSPQMLRTPAPPSGVTPQDPHYIMLLGVEGADVT
GRSTVTKTKLLKCPVDPPALDAPNADLCDSVPVWDRLPCAPSSISQRDCEKVGCCYNLEANSCYYG
NTVTSHCTQDGHFSIVVSRKVTSPPLLLNSVRLAFRNDHECTPVMTTHTFATFWFPLNSCGTTRRI
IGDWVVYENELVATRDVRAWSHGSITRDSIFRLQVSCSYLISSNASQVNVQIFTLPPPLPETQAGP
LTLELKIAKDKHYESYYTASDYPVVKLLRDPIYVEVSIRHRTDPYLGLFLQHCWATPSLNPQHQRQ
WPMLVNGCP

SEQ ID NO. 7 is another partial dog DNA sequence that codes for SEQ ID NO 8.

```
tgctcaggtgtcctaggaatcccccagacccaactttgttatctagcttgagttactctcctgat    (SEQ ID NO:7)
caaaacagagccctagatgttccaaatgctgatctgtgtgactttgtcccagtgtgggacaggct
gccatgtgttccttcacccatcactgaagaagactgcaagaagattggttgctgctacaatttgg
aggtgaatttctgttattatggaaacacagtgacctcccactgtacccaagatggccacttctnn
nnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnggttccgttacccgtgacagtattttcaggctccgagt
tagctgcagctactctataagtagcaatgccttcccagttaatgtccacgtgtttacatttccac
caccgcattctgagacccagcctggaccctcactctggaactcaagattgccaaggataagcac
tatggttcctactacactgctggtgactacccagtggtgaagctacttcgggatcccatttatgt
ggaggtctctatccgccacagaacagaccccacctggggctgctcctccattactgttgggcca
cacccagcagaaacccacagcatcagccccagtggctcatgctggtgaaaggctgcccta
``` where n at positions 259 to 483 corresponds to a gap in the partial dog sequence, and n can be any nucleotide and any one or all of nucleotides 259 to 483 can either be present or absent.

SEQ ID NO: 15 codes for SEQ ID NO:16. These sequences represent a genetically engineered construct consisting of ferret and dog partial ZPB sequences that have been fused together to form a ferret/dog hybrid.

LRCPRNPPDPTLLSSLSYSPDQNRALDVPNADLCDFVPVWDRLPCVPSPITEEDCKKIGCCYNLE (SEQ ID NO:8)

VNFCYYGNTVTSHCTQDGHFXXXXXXXXXXXXXXXXXXXXXXXXXXXXXXXXXXXXXXXXXXXX

XXXXXXXXXXXXXXXXXXXXXXXXXXXXXXXXGSVTRDSIFRLRVSCSYSISSNAFPVNVHVFTFPP

PHSETQPGPLTLELKIAKDKHYGSYYTAGDYPVVKLLRDPIYVEVSIRHRTDPHLGLLLHYCWAT

PSRNPQHQPQWLMLVKGCP where X at positions 86 to 160 corresponds to a gap in the partial dog sequence, and X can be any amino acid and any one or all of residues 86 to 160 can either be present or absent.

SEQ ID NO. 13 is a more complete dog DNA sequence that codes for SEQ ID NO. 14. As compared with SEQ ID NOS: 7 and 8, there are no gaps in SEQ ID NOS. 13 and 14 and the latter sequences encode or contain (respectively) loop 2 as well as loop 1.

(SEQ ID NO 13):

GAGGGCCCAGGAAGCTCCATGGTGTTAGAAGCCTCTTATGATGGCTGCTATGTCACCGAGTGGGTG

AGGACGACTCGATCACCAGAAATGCCGAGACCCCGTGTGTCACCATCAGGGGTGTCTCCCCAGGAC

CCCCACTATGTCATGCTGGTTGGAGTTGAAGGAGCAGATGTGGCTGGACGCAACATGGTTACAAAG

ACACAGCTGCTCAGGTGTCCTATGGATCCCCCAGACCCAACTTTGTTATCTAGCTTGAGTTACTCT

CCTGATCAAAACAGAGCCCTAGATGTTCCAAATGCTGATCTGTGTGACTTTGTCCCAGTGTGGGAC

AGGCTGCCATGTGTTCCTTCACCCATCACTGAAGAAGACTGCAAGAAGATTGGTTGCTGCTACAAT

TTGGAGGTGAATTTCTGTTATTATGGAAACACAGTGACCTCCCACTGTACCCAAGATGGCTACTTC

TACATCGCTGTGTCTCGGAATGTGACCTCACCCCCACTTCTCTTGAATTCTGTGCGCTTGGCCTTC

AGGAATGATGTGGAATGTACCCCTGTGATGGCAACACACACTTTTGCCCTATTCTGGTTTCCATTT

AACTCCTGTGGTACCACAAGACGGATCACTGGAGACCAGGCAGTATATGAAAATGAGCTGGTTGCA

GCTAGAGATGTTAGAACTTGGAGCCATGGTTCTATCACCCGTGACAGTATTTTCAGGCTCCGAGTT

AGCTGCAGCTACTCTATAAGTAGCAATGCCTTCCCAGTTAATGTCCACGTGTTTACATTTCCACCA

CCGCATTCTGAGACCCAGCCTGGACCCCTCACTCTGGAACTCAAGATTGCCAAGGATAAGCACTAT

GGTTCCTACTACACTGCTGGTGACTACCCAGTGGTGAAGCTACTTCGGGATCCCATTTATGTGGAG

GTCTCTATCCGCCACAGAACAGACCCCCACCTGGGGCTGCTCCTCCATTACTGTTGGGCCACACCC

AGCAGAAACCCACAGCATCAGCCCCAGTGGCTCATGCTGGTGAAAGGCTGCCCCTA (SEQ ID NO 14):

EGPGSSMVLEASYDGCYVTEWVRTTRSPEMPRPRVSPSGVSPQDPHYVMLVGVEGADVAGRNMVTK

TQLLRCPMDPPDPTLLSSLSYSPDQNRALDVPNADLCDFVPVWDRLPCVPSPITEEDCKKIGCCYN

LEVNFCYYGNTVTSHCTQDGYFYIAVSRNVTSPPLLLNSVRLAFRNDVECTPVMATHTFALFWFPF

NSCGTTRRITGDQAVYENELVAARDVRTWSHGSITRDSIFRLRVSCSYSISSNAFPVNVHVFTFPP

PHSETQPGPLTLELKIAKDKHYGSYYTAGDYPVVKLLRDPIYVEVSIRHRTDPHLGLLLHYCWATP

SRNPQHQPQWLMLVKGCP (SEQ ID NO 15):

GGCTGCGGTACCTGGGTAAGGGAAGGCCCAGGCAGCTCCATGGTGCTAGAAGCCTCTTACAGCGGC

TGCTATGTCACCGAGTGGGTAAGGACCACCCAATCGCCACAAATGCTGCGAACCCCTGCACCACCA

TCAGGGGTGACTCCCCAGGATCCCCACTATATCATGCTACTTGGAGTTGAAGGAGCAGATGTGACT

GGACGCAGCACGGTTACAAAGACAAAGCTTCTCAGGTGTCCTAGGAATCCCCCAGACCCAACTTTG

TTATCTAGCTTGAGTTACTCTCCTGATCAAAACAGAGCCCTCGAGGCTCCAAACGCTGACCTGTGT

GATTCTGTCCCAGTGTGGGACAGGCTGCCATGTGCTCCTTCATCTATCAGTCAAAGAGATTGTGAG

AAGGTTGGTTGCTGCTACAATTTGGAGGCTAATTCCTGTTACTATGGAAACACAGTGACGTCCCAC

TGTACCCAAGATGGCCACTTCT (SEQ ID NO 16):

GCGTWVREGPGSSMVLEASYSGCYVTEWVRTTQSPQMLRTPAPPSGVTPQDPHYIMLLGVEGADVT

GRSTVTKTKLLRCPRNPPDPTLLSSLSYSPDQNRALEAPNADLCDSVPVWDRLPCAPSSISQRDCE

KVGCCYNLEANSCYYGNTVTSHCTQDGHF

Sequence alignments of some of these fragments with known sequences are set out in FIG. 5. A schematic alignment of some of these sequences in comparison with cat ZPB is set out in FIG. 6.

Recombinant Zona Pellucida Antigens

Three overlapping cat ZPB clones (C1, C2, and C3) were generated to produce recombinant cat ZPB fragments that span the entire length of native cat ZPB (FIG. 7). The C1 clone codes for cat ZPB amino acids 1–192, the C2 clone codes for amino acids 172–340, and the C3 clone codes for amino acids 326–500. Recombinant proteins were produced from clones C1, C2, and C3 in *E. coli* using the T7 expression-based pET32 system (Novagen). Antibodies to all three fragments were generated in rabbits and tested for their ability to reduce fertilization of cat oocytes using an in vitro fertilization assay (Table 1).

Pre-immune serum and sera directed against the three recombinant protein fragments had no significant effect on maturation of cat oocytes. Both anti-C1 and anti-C2 sera reduced fertilization of cat oocytes, in particular anti-C2 serum completely blocked fertilization of all eggs evaluated (0% fertilization). This suggests that sites responsible for sperm binding to oocytes are present on cat ZPB in regions spanned by C1 and C2 and that these sites are blocked by homologous antibody.

Since cat ZP is poorly immunogenic in cats, a cDNA clone consisting of ferret and dog ZPB sequences (labeled FDH) was genetically engineered (SEQ ID NO: 15) and subcloned into the pET32 expression system (Novagen) to produce a fused recombinant protein (SEQ ID NO: 16) for immunization of cats. (For comparative purposes, sequence alignments between cat, dog and ferret ZPB nucleotide sequences and ZPB are set out in FIGS. 8 and 9 respectively.) In this clone, the ferret sequence corresponds to cat ZPB amino acids 71–143 and the dog sequence corresponds to cat ZPB amino acids 144–230. The FDH clone spans regions of the C1 and the C2 fragments combined. This region contains additional sequences (designated loops 1 and 2 in this document) that are unique to cat ZPB. Genbank searches indicated that no other mammalian ZPB is known that contains both these sequences. By combining ferret and dog ZPB sequences, a fused protein (FDH) can be creates that corresponds to this unique region of cat ZPB. Rabbits, mice and cats were immunized with FDH protein to prove immunogenicity and raise antibodies against the fused ferret and dog ZPB fragments (Tables 2, 3 and 4).

The data presented by Tables 2, 3 and 4 clearly show that the ferret/dog recombinant protein (fused to the pET32 tag) is immunogenic in three different mammalian species (rabbits, mice and cats). To determine if the mice and cat antibodies were directed to the FDH portion of the fused recombinant protein (the target), titers of the mice and cat anti-sera were measured again using a FDH recombinant protein fused to a different tag (His tag). In this case, the only common structure is the fused FDH (Tables 5 and 6).

The results presented by Tables 2 to 6 clearly show that three mammalian species are capable of producing antibodies to a recombinant protein containing ferret and dog ZPB sequences. A large proportion of the antibodies produced has affinity for the pET32 tag but a significant proportion of the antibodies is directed against the ferret/dog sequences. Rabbit anti-FDH/pET anti-serum was tested for its ability to block cat sperm binding to cat oocytes. Isolated cat oocytes were incubated with the indicated serum to allow binding of antibodies to the egg surface. Unbound serum components were removed by washing. The oocytes were incubated with capacitated sperm, then, the number of sperm bound to each egg was determined by Hoechst 33258 staining and fluorescence microscopy. Cat oocytes incubated with pre-immune serum bound an average of 39 sperm cells. Oocytes incubated with anti-FDH/pET anti-serum bound significantly fewer sperm (average 3.4 sperm/egg). This indicates that rabbits immunized with FDH/pET produced antibodies specific to the FDH portion of the recombinant protein. These antibodies cross reacted with epitopes present on the cat oocyte surface and significantly reduced sperm binding. Therefore, antigens containing ferret and dog ZPB sequences have the ability of eliciting production of antibodies that bind co cat oocytes, thereby, reducing sperm binding and fertilization.

The data presented clearly show that a component of cat zona pellucida, namely ZPB, contains epitopes required for sperm binding and subsequent fertilization. In vitro fertilization assays with blocking antibodies directed against three polypeptides that span the entire length of cat ZPB revealed that two of the polypeptides corresponding to C1 and C2 (particularly C2) contain epitopes that can be targeted for successful immunocontraception. A fused ferret/dog ZPB sequence containing a pET tag is immunogenic in all species tested. ELISA measurements using a FDH/6His fusion protein indicates that mouse and cat anti-sera to fused FDH contain antibodies that bind specifically to the ferret/dog fused polypeptide. That rabbit anti-sera contains antibodies against the fused ferret/dog sequence was inferred by the ability of rabbit anti-sera to bind to cat ZPB epitopes on the oocyte surface and reduce sperm binding. These data demonstrate chat ZPB antigens based on ferret and dog ZPB sequences can effectively raise antibodies that cross react with native car ZPB, block sperm binding, and consequently reduce cat fertility. Since dog ZPB contains unique sequences that are similar to the corresponding sequences in cat ZPB, one skilled in the art can predict that dog fertility would be reduced by immunization with FDH or other constructs that correspond to the same region of ZPB.

It is apparent to one skilled in the art that many variations on the present invention can be made without departing from the scope or spirit of the invention claimed herein.

TABLE 1

Number of eggs used to determine percent egg maturation and the effect of antisera directed to three cat ZPB fragments (C1, C2 and C3) on in vitro fertilization of cat oocytes.

| Antiserum | Number of eggs | Percent egg maturation | Percent Fertilized |
|---|---|---|---|
| Pre-immune | 53 | 64.2% | 22.6% |
| C1 | 35 | 42.9% | 14.3% |
| C2 | 19 | 42.1% | 0% |
| C3 | 8 | 50.0% | 25.0% |

TABLE 2

Production of antibodies against FDH recombinant protein fused to the pET32 tag and monitored over a period of 6 months. Titers are expressed relative to a rabbit reference anti-serum having high affinity for this pET tag.

| | Titer (% reference serum) Post Immunization (months) | | |
|---|---|---|---|
| Rabbit ID | 3 | 4 | 6 |
| 212 | 207 | 186 | 109 |
| 213 | 157 | 149 | 101 |

TABLE 3

Production of antibodies by mice immunized with FDH recombinant protein fused to the pET32 tag. Control mice were immunized with a placebo vaccine containing no antigen. Titers are expressed as a percent of a rabbit anti-serum having high affinity for the pET32.

| | Titer (% reference serum) Post Immunization (weeks) | |
|---|---|---|
| Mouse ID | 4 | 8 |
| No antigen | | |
| 169 | 0 | 0 |
| 170 | 0 | 0 |
| 171 | 0 | 0 |
| 172 | 0 | 0 |
| FDH antigen | | |
| 185 | 232 | 193 |
| 186 | 131 | 115 |

TABLE 3-continued

Production of antibodies by mice immunized with FDH recombinant protein fused to the pET32 tag. Control mice were immunized with a placebo vaccine containing no antigen. Titers are expressed as a percent of a rabbit anti-serum having high affinity for the pET32.

| | Titer (% reference serum) Post Immunization (weeks) | |
|---|---|---|
| Mouse ID | 4 | 8 |
| 187 | 201 | 265 |
| 188 | 216 | 208 |

TABLE 4

Production of antibodies by cats immunized with FDH recombinant protein fused to the pET32 tag. Titers are expressed as a percent of a reference rabbit anti-serum against native cat ZP.

| | Titer (% reference serum) Post Immunization months) | | |
|---|---|---|---|
| Cat ID | 1 | 2 | 4 |
| H1 | 932 | 1588 | 864 |
| H2 | 1467 | 2139 | 4394 |
| H3 | 1562 | 1867 | 1637 |

TABLE 5

Affinity of mice Janti-sera against FDH recombinant protein fused to the pET32 tag for FDH/pET and FDH/His recombinant proteins. FDH/pET titers are expressed as percent of a reference rabbit anti-Serum with high affinity for the pET32 tag. FDH/His titers are expressed as a percent of anti-FDH/pET titers.

| | Titer (% reference serum) Post Immunization (weeks) 8 | |
|---|---|---|
| Mouse ID | FDH/pET | FDH/His |
| 185 | 193 | 48 |
| 186 | 115 | 34 |
| 187 | 265 | 32 |

TABLE 6

Production of cat antibodies against recombinant FDH fused to pET32 tag. Titers were measured against both FDH/pET and FDH/His recombinant proteins. Titer are expressed as a percent of a reference rabbit anti-serum having high affinity for native cat ZP.

| | Titer (% reference serum) Post Immunization (months) | | | |
|---|---|---|---|---|
| | 1 | | 4 | |
| Cat ID | FDH/pET | FDH/His | FDH/pET | FDH/His |
| H1 | 932 | 44 | 864 | 44 |
| H2 | 1467 | 93 | 4394 | 321 |
| H3 | 1562 | 79 | 1637 | 93 |

TABLE 7

Effect of exposinq cat oocytes to rabbit anti-FDH/pET 32 anti-serum on sperm binding to cat occytes in vitro.

| Antiserum | Number of eggs examined | Number of sperm bound/egg |
| --- | --- | --- |
| Pre-immune serum | 22 | 39.0 |
| FDH | 16 | 3.4 |

REFERENCE

Bradley, M. P., I. Eade, J. Penhale, and P. Bird. 1999. Vaccines for fertility regulation of wild and domestic species. J. Biochem 73:91–101.

Brown, R. G., W. D. Bowen, J. D. Eddington, W. C. Kimmins, M. Mezei, J. L. Parsons and B. Pohajdak. 1997a. Evidence for a long-lasting single administration contraceptive vaccine in wild grey seals. J. Reprod. Immunol. 35: 43–51.

Brown, R. G., W. D. Bowen, J. D. Eddington, W. C. Kimmins, M. Mezei, J. L. Parsons and B. Pohajdak. 1997b. Temporal trends in antibody production in captive grey, harp and hooded seals to a single administration immunocontraceptive vaccine. J. Reprod. Immunol. 35: 53–64.

Brown, R., M. Mezei, B. Pohajdak and W. Kimmins. 2001. Method to prevent fertilisation in mammals by administering a single dose of zona pellucida derived antigens, liposome and Freund's adjuvant. U.S. Pat. No. RE37,224 (Corresponds to Canadian Patent 2,137,363).

Gorman, S. P., J. K. Levy, A. L. Hampton, W. R. Collante, A. L. Harris and R. G. Brown. 2002. Evaluation of a porcine zona pellucida vaccine for the immunocontraception of domestic kittens (*Fells catus*). Theriogenology 58:135–149.

Harlow, E. and D. Lane. 1988. *Antibodies—A Laboratory Manual* (Cold Spring Harbor Laboratory, USA, pp. 96–100).

Harris, J. D., K. T. Hsu and J. S. Podolski. 2000. Materials and Methods for immunocontraception. U.S. Pat. No. 6,027, 727.

Ivanova, M., M. Petrov, D. Klissourska and M. Mollova. 1995. Contraceptive potential of porcine zona pellucida in cats. Theriogenology 43: 969–981.

Kirkpatrick, J. F., J. W. Turner, I. K. Liu, and R. Fayrer-Hoskin. 1996. Applications of pig zona pellucida immunocontraception to wildlife fertility control. J. Reprod. Immunol. 35: 43–51.

Muller, L. I., J. Warren and D. L. Evans. 1997. Theory and practice of immunocontraception in wild mammals. Wildi. Soc. Bull. 26:504–514.

Oogjes, G. 1997. Ethical aspects and dilemmas of fertility control of unwanted wildlife: an animal welfarist's perspective. Reproduct. Fertil. Dev. 9:163–167.

Sacco, A. and E. C. Yurewicz. 1989. Use of the zona pellucida as an immunocontraceptive target antigen. In Dietl, J. (Ed): The mammalian egg coat: structure and function. Berlin, Spinger-Verlag; 128–154.

Willis, P., G. Heusner, R. Warren, D. Kessler, R. Fayrer-Hosken. 1994. Equine immunocontraception using porcine zona pellucida: a method for remote delivery and characterization of the immune response. J. Equine Vet. Sci. 14: 364–370.

SEQUENCE LISTING

```
<160> NUMBER OF SEQ ID NOS: 16

<210> SEQ ID NO 1
<211> LENGTH: 359
<212> TYPE: DNA
<213> ORGANISM: Mustela putorius furo

<400> SEQUENCE: 1
gggtccgtca ctcgggacag tattttcagg cttcaagtta gctgcagcta cttgatcagc      60
agcaatgcct cccaggttaa tgtccagatt tttacgctcc caccacccct tcctgaaacc     120
caggctggac cccttactct ggaactcaag attgccaaag ataagcacta tgaatcctat     180
tacactgcca gtgactaccc agtggtgaag ctgcttcggg atcccattta cgtggaggtg     240
tctatccgcc acagaacaga cccctacctg gggctgttcc tccagcactg ttgggccaca     300
cccagcctaa acccccaaca tcagcgccag tggcccatgc tggtcaatgg ctgccctta     359

<210> SEQ ID NO 2
<211> LENGTH: 119
<212> TYPE: PRT
<213> ORGANISM: Mustela putorius furo

<400> SEQUENCE: 2

Gly Ser Val Thr Arg Asp Ser Ile Phe Arg Leu Gln Val Ser Cys Ser
1               5                   10                  15

Tyr Leu Ile Ser Ser Asn Ala Ser Gln Val Asn Val Gln Ile Phe Thr
            20                  25                  30
```

```
Leu Pro Pro Pro Leu Pro Glu Thr Gln Ala Gly Pro Leu Thr Leu Glu
            35                  40                  45

Leu Lys Ile Ala Lys Asp Lys His Tyr Glu Ser Tyr Tyr Thr Ala Ser
 50                  55                  60

Asp Tyr Pro Val Val Lys Leu Leu Arg Asp Pro Ile Tyr Val Glu Val
 65                  70                  75                  80

Ser Ile Arg His Arg Thr Asp Pro Tyr Leu Gly Leu Phe Leu Gln His
                 85                  90                  95

Cys Trp Ala Thr Pro Ser Leu Asn Pro Gln His Gln Arg Gln Trp Pro
                100                 105                 110

Met Leu Val Asn Gly Cys Pro
            115

<210> SEQ ID NO 3
<211> LENGTH: 359
<212> TYPE: DNA
<213> ORGANISM: dog

<400> SEQUENCE: 3
ggttccgtta cccgtgacag tattttcagg ctccgagtta gctgcagcta ctctataagt      60
agcaatgcct tcccagttaa tgtccacgtg tttacatttc caccaccgca ttctgagacc     120
cagcctggac ccctcactct ggaactcaag attgccaagg ataagcacta tggttcctac     180
tacactgctg gtgactaccc agtggtgaag ctacttcggg atcccattta tgtggaggtc     240
tctatccgcc acagaacaga ccccacctg gggctgctcc tccattactg ttgggccaca     300
cccagcagaa acccacagca tcagccccag tggctcatgc tggtgaaagg ctgcccta      359

<210> SEQ ID NO 4
<211> LENGTH: 119
<212> TYPE: PRT
<213> ORGANISM: dog

<400> SEQUENCE: 4

Gly Ser Val Thr Arg Asp Ser Ile Phe Arg Leu Arg Val Ser Cys Ser
 1               5                  10                  15

Tyr Ser Ile Ser Ser Asn Ala Phe Pro Val Asn Val His Val Phe Thr
                20                  25                  30

Phe Pro Pro Pro His Ser Glu Thr Gln Pro Gly Pro Leu Thr Leu Glu
            35                  40                  45

Leu Lys Ile Ala Lys Asp Lys His Tyr Gly Ser Tyr Tyr Thr Ala Gly
 50                  55                  60

Asp Tyr Pro Val Val Lys Leu Leu Arg Asp Pro Ile Tyr Val Glu Val
 65                  70                  75                  80

Ser Ile Arg His Arg Thr Asp Pro His Leu Gly Leu Leu Leu His Tyr
                 85                  90                  95

Cys Trp Ala Thr Pro Ser Arg Asn Pro Gln His Gln Pro Gln Trp Leu
                100                 105                 110

Met Leu Val Lys Gly Cys Pro
            115

<210> SEQ ID NO 5
<211> LENGTH: 1019
<212> TYPE: DNA
<213> ORGANISM: Mustela putorius furo

<400> SEQUENCE: 5
```

```
ggctgcggta cctgggtaag ggaaggccca ggcagctcca tggtgctaga agcctcttac      60
agcggctgct atgtcaccga gtgggtaagg accacccaat cgccacaaat gctgcgaacc     120
cctgcaccac catcagggt gactccccag gatcccact atatcatgct acttggagtt      180
gaaggagcag atgtgactgg acgcagcacg gttacaaaga caaagctgct taagtgtcct     240
gtggatcccc cagccctaga tgctccaaac gctgacctgt gtgattctgt cccagtgtgg     300
gacaggctgc catgtgctcc ttcatctatc agtcaaagag attgtgagaa ggttggttgc     360
tgctacaatt tggaggctaa ttcctgttac tatggaaaca cagtgacgtc ccactgtacc     420
caagatggcc acttctccat tgtcgtgtct cggaaggtga cctcaccccc actgctctta     480
aattctgtgc gcttggcctt caggaatgac catgaatgca cccctgtgat gacaacacac     540
acctttgcca ccttttggtt tccattaaat tcctgtggta ccacaagacg gatcattgga     600
gactgggtag tatatgaaaa tgagctggtc gcaactagag atgtgagagc ttggagccat     660
ggttctatca cccgtgacag tatttcagg cttcaagtta gctgcagcta cttgatcagc     720
agcaatgcct cccaggttaa tgtccagatt tttacgctcc caccacccct tcctgaaacc     780
caggctggac cccttactct ggaactcaag attgccaaag ataagcacta tgaatcctat     840
tacactgcca gtgactaccc agtggtgaag ctgcttcggg atcccattta cgtggaggtg     900
tctatccgcc acagaacaga cccctacctg gggctgttcc tccagcactg ttgggccaca     960
cccagcctaa accccaaca tcagcgccag tggcccatgc tggtcaatgg ctgcccctta    1019
```

<210> SEQ ID NO 6
<211> LENGTH: 339
<212> TYPE: PRT
<213> ORGANISM: Mustela putorius furo

<400> SEQUENCE: 6

```
Gly Cys Gly Thr Trp Val Arg Glu Gly Pro Gly Ser Ser Met Val Leu
1               5                   10                  15

Glu Ala Ser Tyr Ser Gly Cys Tyr Val Thr Glu Trp Val Arg Thr Thr
            20                  25                  30

Gln Ser Pro Gln Met Leu Arg Thr Pro Ala Pro Pro Ser Gly Val Thr
        35                  40                  45

Pro Gln Asp Pro His Tyr Ile Met Leu Leu Gly Val Glu Gly Ala Asp
    50                  55                  60

Val Thr Gly Arg Ser Thr Val Thr Lys Thr Lys Leu Leu Lys Cys Pro
65                  70                  75                  80

Val Asp Pro Pro Ala Leu Asp Ala Pro Asn Ala Asp Leu Cys Asp Ser
                85                  90                  95

Val Pro Val Trp Asp Arg Leu Pro Cys Ala Pro Ser Ser Ile Ser Gln
            100                 105                 110

Arg Asp Cys Glu Lys Val Gly Cys Cys Tyr Asn Leu Glu Ala Asn Ser
        115                 120                 125

Cys Tyr Tyr Gly Asn Thr Val Thr Ser His Cys Thr Gln Asp Gly His
    130                 135                 140

Phe Ser Ile Val Val Ser Arg Lys Val Thr Ser Pro Leu Leu Leu
145                 150                 155                 160

Asn Ser Val Arg Leu Ala Phe Arg Asn Asp His Glu Cys Thr Pro Val
                165                 170                 175

Met Thr Thr His Thr Phe Ala Thr Phe Trp Phe Pro Leu Asn Ser Cys
            180                 185                 190
```

```
Gly Thr Thr Arg Arg Ile Ile Gly Asp Trp Val Val Tyr Glu Asn Glu
            195                 200                 205

Leu Val Ala Thr Arg Asp Val Arg Ala Trp Ser His Gly Ser Ile Thr
        210                 215                 220

Arg Asp Ser Ile Phe Arg Leu Gln Val Ser Cys Ser Tyr Leu Ile Ser
225                 230                 235                 240

Ser Asn Ala Ser Gln Val Asn Val Gln Ile Phe Thr Leu Pro Pro Pro
                245                 250                 255

Leu Pro Glu Thr Gln Ala Gly Pro Leu Thr Leu Glu Leu Lys Ile Ala
            260                 265                 270

Lys Asp Lys His Tyr Glu Ser Tyr Tyr Thr Ala Ser Asp Tyr Pro Val
        275                 280                 285

Val Lys Leu Leu Arg Asp Pro Ile Tyr Val Glu Val Ser Ile Arg His
    290                 295                 300

Arg Thr Asp Pro Tyr Leu Gly Leu Phe Leu Gln His Cys Trp Ala Thr
305                 310                 315                 320

Pro Ser Leu Asn Pro Gln His Gln Arg Gln Trp Pro Met Leu Val Asn
                325                 330                 335

Gly Cys Pro

<210> SEQ ID NO 7
<211> LENGTH: 842
<212> TYPE: DNA
<213> ORGANISM: Mustela putorius furo
<220> FEATURE:
<221> NAME/KEY: misc_feature
<222> LOCATION: (259)..(483)
<223> OTHER INFORMATION: where n at positions 259 to 483 corresponds to
      a gap in the partial dog sequence, and n can be any nucleotide and
      any one or all of nucleotides 259 to 483 can either be present or
      absent

<400> SEQUENCE: 7
tgctcaggtg tcctaggaat cccccagacc caactttgtt atctagcttg agttactctc      60
ctgatcaaaa cagagcccta gatgttccaa atgctgatct gtgtgacttt gtcccagtgt     120
gggacaggct gccatgtgtt ccttcaccca tcactgaaga agactgcaag aagattggtt     180
gctgctacaa tttggaggtg aatttctgtt attatggaaa cacagtgacc tcccactgta     240
cccaagatgg ccacttctnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnggttccg ttacccgtga cagtattttc aggctccgag ttagctgcag ctactctata     540
agtagcaatg ccttcccagt taatgtccac gtgtttacat ttccaccacc gcattctgag     600
acccagcctg gacccctcac tctggaactc aagattgcca aggataagca ctatggttcc     660
tactacactg ctggtgacta cccagtggtg aagctacttc gggatcccat ttatgtggag     720
gtctctatcc gccacagaac agaccccac ctggggctgc tcctccatta ctgttgggcc     780
acacccagca gaaacccaca gcatcagccc cagtggctca tgctggtgaa aggctgcccc     840
ta                                                                    842

<210> SEQ ID NO 8
<211> LENGTH: 279
<212> TYPE: PRT
```

<213> ORGANISM: Mustela putorius furo
<220> FEATURE:
<221> NAME/KEY: SITE
<222> LOCATION: (86)..(160)
<223> OTHER INFORMATION: where Xaa at positions 86 to 160 corresponds to a gap in the partial dog sequence, and Xaa can be any amino acid and any one or all of residues 86 to 160 can either be present or absent

<400> SEQUENCE: 8

```
Leu Arg Cys Pro Arg Asn Pro Pro Asp Pro Thr Leu Leu Ser Ser Leu
1               5                   10                  15

Ser Tyr Ser Pro Asp Gln Asn Arg Ala Leu Asp Val Pro Asn Ala Asp
            20                  25                  30

Leu Cys Asp Phe Val Pro Val Trp Asp Arg Leu Pro Cys Val Pro Ser
        35                  40                  45

Pro Ile Thr Glu Glu Asp Cys Lys Lys Ile Gly Cys Tyr Asn Leu
    50                  55                  60

Glu Val Asn Phe Cys Tyr Tyr Gly Asn Thr Val Thr Ser His Cys Thr
65                  70                  75                  80

Gln Asp Gly His Phe Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa
145                 150                 155                 160

Gly Ser Val Thr Arg Asp Ser Ile Phe Arg Leu Arg Val Ser Cys Ser
                165                 170                 175

Tyr Ser Ile Ser Ser Asn Ala Phe Pro Val Asn Val His Val Phe Thr
            180                 185                 190

Phe Pro Pro His Ser Glu Thr Gln Pro Gly Pro Leu Thr Leu Glu
        195                 200                 205

Leu Lys Ile Ala Lys Asp Lys His Tyr Gly Ser Tyr Tyr Thr Ala Gly
    210                 215                 220

Asp Tyr Pro Val Val Lys Leu Leu Arg Asp Pro Ile Tyr Val Glu Val
225                 230                 235                 240

Ser Ile Arg His Arg Thr Asp Pro His Leu Gly Leu Leu His Tyr
                245                 250                 255

Cys Trp Ala Thr Pro Ser Arg Asn Pro Gln His Gln Pro Gln Trp Leu
            260                 265                 270

Met Leu Val Lys Gly Cys Pro
        275
```

<210> SEQ ID NO 9
<211> LENGTH: 534
<212> TYPE: PRT
<213> ORGANISM: cow

<400> SEQUENCE: 9

```
Met Trp Leu Leu Leu Gln Leu Val Trp Leu Cys Phe Leu Leu Ser Leu
1               5                   10                  15

Gly Leu Asn Ser Trp His Gln Ser Lys Val Pro Glu Tyr Pro Asp Glu
            20                  25                  30
```

```
Leu Arg Cys Gly Leu Arg Ser Phe Gln Phe Thr Ile Asn Pro Leu Ser
        35                  40                  45

Gln Glu Thr Glu Thr Pro Pro Val Leu Val Ala Trp Asp Asn His Gly
 50                  55                  60

Leu Pro His Ser Leu Gln Asn Asp Ser Asp Cys Gly Thr Trp Val Ser
 65                  70                  75                  80

Glu Gly Pro Gly Ser Ser Leu Val Gly Glu Ala Ser Tyr Ser Gly Cys
                 85                  90                  95

Tyr Val Thr Glu Trp Glu Ser Tyr Tyr Ile Met Thr Val Gly Ile Glu
            100                 105                 110

Arg Ala Gly Val Ser Gly Ser Gly Ala Phe Ile Glu Thr Lys Leu Phe
            115                 120                 125

Lys Cys Pro Val Asn Leu Pro Asp Val Pro Asn Ala Gly Leu Cys Asp
130                 135                 140

Ser Val Pro Val Trp Asp Arg Leu Pro Cys Ala Pro Ser Pro Ile Thr
145                 150                 155                 160

Gln Gly Asp Cys Lys Gln Leu Gly Cys Cys Tyr Asn Ser Glu Glu Val
                165                 170                 175

Ile Ser Cys Tyr Tyr Gly Asn Thr Val Thr Ser His Cys Thr Gln Asp
            180                 185                 190

Gly His Phe Ser Ile Ala Val Ser Arg Asn Val Thr Ser Pro Pro Leu
            195                 200                 205

Leu Leu Asn Ser Val His Leu Ala Phe Arg Asn Asp Ser Glu Cys Lys
            210                 215                 220

Pro Val Met Ala Thr His Thr Phe Val Leu Phe Arg Phe Pro Phe Thr
225                 230                 235                 240

Thr Cys Gly Thr Thr Lys Gln Ile Thr Gly Lys Gln Ala Val Tyr Glu
                245                 250                 255

Asn Glu Leu Val Ala Ala Arg Asp Val Arg Thr Trp Ser Arg Gly Ser
            260                 265                 270

Ile Thr Arg Asp Ser Thr Phe Arg Leu Gln Val Ser Cys Ser Tyr Ser
            275                 280                 285

Ala Ser Ser Ala Leu Pro Val Asn Val Gln Val Leu Thr Leu Pro
            290                 295                 300

Pro Pro Leu Pro Glu Thr Gln Pro Gly Asn Leu Thr Leu Glu Leu Lys
305                 310                 315                 320

Ile Ala Lys Asp Lys Arg Tyr Arg Ser Tyr Tyr Thr Ala Ser Asp Tyr
                325                 330                 335

Pro Val Val Lys Leu Leu Arg Asp Pro Ile Tyr Val Glu Val Ser Ile
            340                 345                 350

His Gln Arg Thr Asp Pro Ser Leu Glu Leu Arg Leu Asp Gln Cys Trp
            355                 360                 365

Ala Thr Pro Gly Ala Asp Ala Leu Leu Gln Pro Gln Trp Pro Leu Leu
            370                 375                 380

Val Asn Gly Cys Pro Tyr Thr Gly Asp Asn Tyr Gln Thr Lys Leu Ile
385                 390                 395                 400

Pro Val Trp Glu Ala Ser Asp Leu Pro Phe Pro Ser His Tyr Gln Arg
                405                 410                 415

Phe Ser Ile Ser Thr Phe Ser Phe Val Asp Ser Val Ala Lys Arg Ala
            420                 425                 430

Leu Lys Gly Pro Val Tyr Leu His Cys Ser Ala Ser Val Cys Gln Pro
            435                 440                 445
```

```
Ala Gly Thr Pro Ser Cys Val Thr Leu Cys Pro Ala Arg Arg Arg Arg
    450                 455                 460

Ser Ser Asp Ile His Phe Gln Asn Asn Thr Ala Ser Ile Ser Ser Lys
465                 470                 475                 480

Gly Pro Leu Ile Leu Leu Gln Ala Ile Gln Asp Ser Ser Glu Lys Leu
                485                 490                 495

His Lys Tyr Ser Arg Ser Pro Val Asp Ser Gln Ala Leu Trp Val Ala
                500                 505                 510

Gly Leu Ser Gly Ile Leu Ile Val Gly Ala Leu Phe Met Ser Tyr Leu
            515                 520                 525

Ala Ile Arg Lys Trp Arg
    530

<210> SEQ ID NO 10
<211> LENGTH: 536
<212> TYPE: PRT
<213> ORGANISM: pig

<400> SEQUENCE: 10

Met Trp Leu Arg Pro Ser Ile Trp Leu Cys Phe Pro Leu Cys Leu Ala
1               5                   10                  15

Leu Pro Gly Gln Ser Gln Pro Lys Ala Ala Asp Asp Leu Gly Gly Leu
            20                  25                  30

Tyr Cys Gly Pro Ser Ser Phe His Phe Ser Ile Asn Leu Leu Ser Gln
        35                  40                  45

Asp Thr Ala Thr Pro Pro Ala Leu Val Val Trp Asp Arg Arg Gly Arg
    50                  55                  60

Leu His Lys Leu Gln Asn Asp Ser Gly Cys Gly Thr Trp Val His Lys
65                  70                  75                  80

Gly Pro Gly Ser Ser Met Gly Val Glu Ala Ser Tyr Arg Gly Cys Tyr
                85                  90                  95

Val Thr Glu Trp Asp Ser His Tyr Leu Met Pro Ile Gly Leu Glu Glu
            100                 105                 110

Ala Asp Ala Gly Gly His Arg Thr Val Thr Glu Thr Lys Leu Phe Lys
        115                 120                 125

Cys Pro Val Asp Phe Leu Ala Leu Asp Val Pro Thr Ile Gly Leu Cys
    130                 135                 140

Asp Ala Val Pro Val Trp Asp Arg Leu Pro Cys Ala Pro Pro Pro Ile
145                 150                 155                 160

Thr Gln Gly Glu Cys Lys Gln Leu Gly Cys Cys Tyr Asn Ser Glu Glu
                165                 170                 175

Val Pro Ser Cys Tyr Tyr Gly Asn Thr Val Thr Ser Arg Cys Thr Gln
            180                 185                 190

Asp Gly His Phe Ser Ile Ala Val Ser Arg Asn Val Thr Ser Pro Pro
        195                 200                 205

Leu Leu Trp Asp Ser Val His Leu Ala Phe Arg Asn Asp Ser Glu Cys
    210                 215                 220

Lys Pro Val Met Glu Thr His Thr Phe Val Leu Phe Arg Phe Pro Phe
225                 230                 235                 240

Ser Ser Cys Gly Thr Ala Lys Arg Val Thr Gly Asn Gln Ala Val Tyr
                245                 250                 255

Glu Asn Glu Leu Val Ala Ala Arg Asp Val Arg Thr Trp Ser His Gly
            260                 265                 270
```

```
Ser Ile Thr Arg Asp Ser Ile Phe Arg Leu Arg Val Ser Cys Ile Tyr
        275                 280                 285

Ser Val Ser Ser Ser Ala Leu Pro Val Asn Ile Gln Val Phe Thr Leu
        290                 295                 300

Pro Pro Pro Leu Pro Glu Thr His Pro Gly Pro Leu Thr Leu Glu Leu
305                 310                 315                 320

Gln Ile Ala Lys Asp Glu Arg Tyr Gly Ser Tyr Tyr Asn Ala Ser Asp
                325                 330                 335

Tyr Pro Val Val Lys Leu Leu Arg Glu Pro Ile Tyr Val Glu Val Ser
                340                 345                 350

Ile Arg His Arg Thr Asp Pro Ser Leu Gly Leu His Leu His Gln Cys
                355                 360                 365

Trp Ala Thr Pro Gly Met Ser Pro Leu Leu Gln Pro Gln Trp Pro Met
            370                 375                 380

Leu Val Asn Gly Cys Pro Tyr Thr Gly Asp Asn Tyr Gln Thr Lys Leu
385                 390                 395                 400

Ile Pro Val Gln Lys Ala Ser Asn Leu Leu Phe Pro Ser His Tyr Gln
                405                 410                 415

Arg Phe Ser Val Ser Thr Phe Ser Phe Val Asp Ser Val Ala Lys Gln
                420                 425                 430

Ala Leu Lys Gly Pro Val Tyr Leu His Cys Thr Ala Ser Val Cys Lys
                435                 440                 445

Pro Ala Gly Ala Pro Ile Cys Val Thr Thr Cys Pro Ala Ala Arg Arg
450                 455                 460

Arg Arg Ser Ser Asp Ile His Phe Gln Asn Gly Thr Ala Ser Ile Ser
465                 470                 475                 480

Ser Lys Gly Pro Met Ile Leu Leu Gln Ala Thr Arg Asp Ser Ser Glu
                485                 490                 495

Arg Leu His Lys Tyr Ser Arg Pro Pro Val Asp Ser His Ala Leu Trp
                500                 505                 510

Val Ala Gly Leu Leu Gly Ser Leu Ile Ile Gly Ala Leu Leu Val Ser
            515                 520                 525

Tyr Leu Val Phe Arg Lys Trp Arg
        530                 535

<210> SEQ ID NO 11
<211> LENGTH: 570
<212> TYPE: PRT
<213> ORGANISM: cat

<400> SEQUENCE: 11

Met Trp Leu Leu Gln Pro Leu Leu Leu Cys Val Pro Leu Ser Leu Ala
1               5                   10                  15

Val His Gly Gln Gln Lys Pro Gln Val Pro Asp Tyr Pro Gly Glu Leu
                20                  25                  30

His Cys Gly Leu Gln Ser Leu Gln Phe Ala Ile Asn Pro Ser Pro Gly
            35                  40                  45

Lys Ala Thr Pro Ala Leu Ile Val Trp Asp Asn Arg Gly Leu Pro His
        50                  55                  60

Lys Leu Gln Asn Asn Ser Gly Cys Gly Thr Trp Val Arg Glu Ser Pro
65                  70                  75                  80

Gly Gly Ser Val Leu Leu Asp Ala Ser Tyr Ser Ser Cys Tyr Val Asn
                85                  90                  95
```

```
Glu Trp Val Ser Thr Thr Gln Ser Pro Gly Thr Ser Arg Pro Pro Thr
            100                 105                 110

Pro Ala Ser Arg Val Thr Pro Gln Asp Ser His Tyr Val Met Ile Val
        115                 120                 125

Gly Val Glu Gly Thr Asp Ala Ala Gly Arg Val Thr Asn Thr Lys
    130                 135                 140

Val Leu Arg Cys Pro Arg Asn Pro Pro Asp Gln Ala Leu Val Ser Ser
145                 150                 155                 160

Leu Ser Pro Ser Pro Leu Gln Asn Val Ala Leu Glu Ala Pro Asn Ala
                165                 170                 175

Asp Leu Cys Asp Ser Val Pro Lys Trp Asp Arg Leu Pro Cys Ala Ser
            180                 185                 190

Ser Pro Ile Thr Gln Gly Asp Cys Asn Lys Leu Gly Cys Cys Tyr Lys
            195                 200                 205

Ser Glu Ala Asn Ser Cys Tyr Tyr Gly Asn Thr Val Thr Ser Arg Cys
    210                 215                 220

Thr Gln Asp Gly His Phe Ser Ile Ala Val Ser Arg Asn Val Thr Ser
225                 230                 235                 240

Pro Pro Leu Leu Leu Asn Ser Leu Arg Leu Ala Phe Gly Lys Asp Arg
                245                 250                 255

Glu Cys Asn Pro Val Lys Ala Thr Arg Ala Phe Ala Leu Phe Phe Phe
            260                 265                 270

Pro Phe Asn Ser Cys Gly Thr Thr Arg Trp Val Thr Gly Asp Gln Ala
        275                 280                 285

Val Tyr Glu Asn Glu Leu Val Ala Ala Arg Asp Val Arg Thr Trp Ser
    290                 295                 300

His Gly Ser Ile Thr Arg Asp Ser Ile Phe Arg Leu Arg Val Ser Cys
305                 310                 315                 320

Ser Tyr Ser Val Arg Ser Asn Ala Phe Pro Leu Ser Val Gln Val Phe
                325                 330                 335

Thr Ile Pro Pro Pro His Leu Lys Thr Gln His Gly Pro Leu Thr Leu
            340                 345                 350

Glu Leu Lys Ile Ala Lys Asp Lys His Tyr Gly Ser Tyr Tyr Thr Ile
        355                 360                 365

Gly Asp Tyr Pro Val Val Lys Leu Leu Arg Asp Pro Ile Tyr Val Glu
    370                 375                 380

Val Ser Ile Arg His Arg Thr Asp Pro Ser Leu Gly Leu Leu Leu His
385                 390                 395                 400

Asn Cys Trp Ala Thr Pro Gly Lys Asn Ser Gln Ser Leu Ser Gln Trp
                405                 410                 415

Pro Ile Leu Val Lys Gly Cys Pro Tyr Val Gly Asp Asn Tyr Gln Thr
            420                 425                 430

Gln Leu Ile Pro Val Gln Lys Ala Leu Asp Thr Pro Phe Pro Ser Tyr
        435                 440                 445

Tyr Lys Arg Phe Ser Ile Phe Thr Phe Ser Phe Val Asp Thr Met Ala
    450                 455                 460

Lys Trp Ala Leu Arg Gly Pro Val Tyr Leu His Cys Asn Val Ser Ile
465                 470                 475                 480

Cys Gln Pro Ala Gly Thr Ser Ser Cys Arg Ile Thr Cys Pro Val Ala
                485                 490                 495

Arg Arg Arg Arg His Ser Asp Leu His His His Ser Ser Thr Ala Ser
            500                 505                 510
```

```
Ile Ser Ser Lys Gly Pro Met Ile Leu Leu Gln Ala Thr Met Asp Ser
        515                 520                 525

Ala Glu Lys Leu His Lys Asn Ser Ser Pro Ile Asp Ser Gln Ala
    530                 535                 540

Leu Trp Met Ala Gly Leu Ser Gly Thr Leu Ile Phe Gly Phe Leu Leu
545                 550                 555                 560

Val Ser Tyr Leu Ala Ile Arg Lys Arg Arg
                565                 570

<210> SEQ ID NO 12
<211> LENGTH: 136
<212> TYPE: PRT
<213> ORGANISM: Mustela putorius furo
<220> FEATURE:
<221> NAME/KEY: MISC_FEATURE
<222> LOCATION: (90)..(90)
<223> OTHER INFORMATION: X = any amino acid

<400> SEQUENCE: 12

Pro Gly Ser Ser Met Val Leu Glu Ala Ser Tyr Ser Gly Cys Tyr Val
1               5                   10                  15

Thr Glu Trp Val Arg Thr Thr Gln Ser Pro Gln Met Leu Arg Thr Pro
            20                  25                  30

Ala Pro Pro Ser Gly Val Thr Pro Gln Asp Pro His Tyr Ile Met Leu
        35                  40                  45

Leu Gly Val Glu Gly Ala Asp Val Thr Gly Arg Ser Thr Val Thr Lys
    50                  55                  60

Thr Lys Leu Leu Lys Cys Pro Val Asp Pro Pro Ala Leu Asp Ala Pro
65                  70                  75                  80

Asn Ala Asp Leu Cys Asp Ser Val Pro Xaa Trp Asp Arg Leu Pro Cys
                85                  90                  95

Ala Pro Ser Ser Ile Ser Gln Arg Asp Cys Glu Lys Val Gly Cys Cys
            100                 105                 110

Tyr Asn Leu Glu Ala Asn Ser Cys Tyr Tyr Gly Asn Thr Val Thr Ser
        115                 120                 125

His Cys Thr Gln Asp Gly His Phe
    130                 135

<210> SEQ ID NO 13
<211> LENGTH: 1046
<212> TYPE: DNA
<213> ORGANISM: Canis familiaris

<400> SEQUENCE: 13
gagggcccag gaagctccat ggtgttagaa gcctcttatg atggctgcta tgtcaccgag      60
tgggtgagga cgactcgatc accagaaatg ccgagacccc gtgtgtcacc atcagggggtg     120 tctccccagg accccactc tgtcatgctg gttggagttg aaggagcaga gtgggctgga     180
cgcaacatgg ttacaaagac acagctgctc aggtgtccta tggatccccc agacccaact    240
ttgttatcta gcttgagtta ctctcctgat caaaacagag ccctagatgt tccaaatgct    300
gatctgtgtg actttgtccc agtgtgggac aggctgccat gtgttccttc acccatcact    360
gaagaagact gcaagaagat tggttgctgc tacaatttgg aggtgaattt ctgttattat    420
ggaaacacag tgacctccca ctgtacccaa gatggctact tctacatcgc tgtgtctcgg    480
aatgtgacct caccccact tctcttgaat tctgtgcgct tggccttcag gaatgatgtg    540
gaatgtaccc ctgtgatggc aacacacact ttgcccctat tctggtttcc atttaactcc    600
```

```
tgtggtacca caagacggat cactggagac caggcagtat atgaaaatga gctggttgca    660
gctagagatg ttagaacttg agccatggt tctatcaccc gtgacagtat tttcaggctc    720
cgagttagct gcagctactc tataagtagc aatgccttcc cagttaatgt ccacgtgttt    780
acatttccac caccgcattc tgagacccag cctggacccc tcactctgga actcaagatt    840
gccaaggata agcactatgg ttcctactac actgctggtg actacccagt ggtgaagcta    900
cttcgggatc ccatttatgt ggaggtctct atccgccaca gaacagaccc ccacctgggg    960
ctgctcctcc attactgttg ggccacaccc agcagaaacc cacagcatca gccccagtgg   1020
ctcatgctgg tgaaaggctg ccccta                                         1046
```

<210> SEQ ID NO 14
<211> LENGTH: 348
<212> TYPE: PRT
<213> ORGANISM: Canis familiaris

<400> SEQUENCE: 14

```
Glu Gly Pro Gly Ser Ser Met Val Leu Glu Ala Ser Tyr Asp Gly Cys
1               5                   10                  15

Tyr Val Thr Glu Trp Val Arg Thr Thr Arg Ser Pro Glu Met Pro Arg
            20                  25                  30

Pro Arg Val Ser Pro Ser Gly Val Ser Pro Gln Asp Pro His Tyr Val
        35                  40                  45

Met Leu Val Gly Val Glu Gly Ala Asp Val Ala Gly Arg Asn Met Val
    50                  55                  60

Thr Lys Thr Gln Leu Leu Arg Cys Pro Met Asp Pro Pro Asp Pro Thr
65                  70                  75                  80

Leu Leu Ser Ser Leu Ser Tyr Ser Pro Asp Gln Asn Arg Ala Leu Asp
                85                  90                  95

Val Pro Asn Ala Asp Leu Cys Asp Phe Val Pro Val Trp Asp Arg Leu
            100                 105                 110

Pro Cys Val Pro Ser Pro Ile Thr Glu Glu Asp Cys Lys Lys Ile Gly
        115                 120                 125

Cys Cys Tyr Asn Leu Glu Val Asn Phe Cys Tyr Tyr Gly Asn Thr Val
    130                 135                 140

Thr Ser His Cys Thr Gln Asp Gly Tyr Phe Tyr Ile Ala Val Ser Arg
145                 150                 155                 160

Asn Val Thr Ser Pro Pro Leu Leu Leu Asn Ser Val Arg Leu Ala Phe
                165                 170                 175

Arg Asn Asp Val Glu Cys Thr Pro Val Met Ala Thr His Thr Phe Ala
            180                 185                 190

Leu Phe Trp Phe Pro Phe Asn Ser Cys Gly Thr Thr Arg Arg Ile Thr
        195                 200                 205

Gly Asp Gln Ala Val Tyr Glu Asn Glu Leu Val Ala Ala Arg Asp Val
    210                 215                 220

Arg Thr Trp Ser His Gly Ser Ile Thr Arg Asp Ser Ile Phe Arg Leu
225                 230                 235                 240

Arg Val Ser Cys Ser Tyr Ser Ile Ser Ser Asn Ala Phe Pro Val Asn
                245                 250                 255

Val His Val Phe Thr Phe Pro Pro His Ser Glu Thr Gln Pro Gly
            260                 265                 270

Pro Leu Thr Leu Glu Leu Lys Ile Ala Lys Asp Lys His Tyr Gly Ser
        275                 280                 285
```

```
Tyr Tyr Thr Ala Gly Asp Tyr Pro Val Val Lys Leu Leu Arg Asp Pro
    290                 295                 300
Ile Tyr Val Glu Val Ser Ile Arg His Arg Thr Asp Pro His Leu Gly
305                 310                 315                 320
Leu Leu Leu His Tyr Cys Trp Ala Thr Pro Ser Arg Asn Pro Gln His
                325                 330                 335
Gln Pro Gln Trp Leu Met Leu Val Lys Gly Cys Pro
            340                 345
```

<210> SEQ ID NO 15
<211> LENGTH: 484
<212> TYPE: DNA
<213> ORGANISM: Artificial
<220> FEATURE:
<223> OTHER INFORMATION: Ferret/dog hybrid

<400> SEQUENCE: 15

```
ggctgcggta cctgggtaag ggaaggccca ggcagctcca tggtgctaga agcctcttac      60
agcggctgct atgtcaccga gtgggtaagg accacccaat cgccacaaat gctgcgaacc     120
cctgcaccac catcagggt gactccccag gatccccact atatcatgct acttggagtt     180
gaaggagcag atgtgactgg acgcagcacg gttacaaaga caaagcttct caggtgtcct     240
aggaatcccc cagacccaac tttgttatct agcttgagtt actctcctga tcaaaacaga     300
gccctcgagg ctccaaacgc tgacctgtgt gattctgtcc cagtgtggga caggctgcca     360
tgtgctcctt catctatcag tcaaagagat tgtgagaagg ttggttgctg ctacaatttg     420
gaggctaatt cctgttacta tggaaacaca gtgacgtccc actgtaccca agatggccac     480
ttct                                                                  484
```

<210> SEQ ID NO 16
<211> LENGTH: 161
<212> TYPE: PRT
<213> ORGANISM: Artificial
<220> FEATURE:
<223> OTHER INFORMATION: Ferret/dog hybrid

<400> SEQUENCE: 16

```
Gly Cys Gly Thr Trp Val Arg Glu Gly Pro Gly Ser Ser Met Val Leu
1               5                   10                  15
Glu Ala Ser Tyr Ser Gly Cys Tyr Val Thr Glu Trp Val Arg Thr Thr
            20                  25                  30
Gln Ser Pro Gln Met Leu Arg Thr Pro Ala Pro Pro Ser Gly Val Thr
        35                  40                  45
Pro Gln Asp Pro His Tyr Ile Met Leu Leu Gly Val Glu Gly Ala Asp
    50                  55                  60
Val Thr Gly Arg Ser Thr Val Thr Lys Thr Lys Leu Leu Arg Cys Pro
65                  70                  75                  80
Arg Asn Pro Pro Asp Pro Thr Leu Leu Ser Ser Leu Ser Tyr Ser Pro
                85                  90                  95
Asp Gln Asn Arg Ala Leu Glu Ala Pro Asn Ala Asp Leu Cys Asp Ser
            100                 105                 110
Val Pro Val Trp Asp Arg Leu Pro Cys Ala Pro Ser Ser Ile Ser Gln
        115                 120                 125
Arg Asp Cys Glu Lys Val Gly Cys Cys Tyr Asn Leu Glu Ala Asn Ser
    130                 135                 140
```

```
Cys Tyr Tyr Gly Asn Thr Val Thr Ser His Cys Thr Gln Asp Gly His
145                 150             155                 160
Phe
```

The invention claimed is:

1. An isolated polypeptide comprising an amino acid sequence selected from the group consisting of:
   (a) SEQ ID NO: 14; and
   (b) a fragment SEQ ID NO: 14, where said fragment elicits an immune response to a polypeptide of SEQ ID NO: 14, said fragment selected from the group consisting of:
   at least 20 contiguous amino acids of SEQ ID NO:14 from amino acid 1 to amino acid 116; and
   at least 44 contiguous amino acids of SEQ ID NO:14 from amino acid 96 to amino acid 264.

2. A composition comprising the polypeptide according to claim 1 and a carrier or diluent suitable for use in a vaccine.

3. A kit for inducing infertility in a mammal comprising the polypeptide according to claim 1 and instructions for its use in eliciting an immune response against native zona pellucida in a mammal.

4. A method for inducing anti-ZPB antibodies in a mammal, the method comprising administering to the mammal at least one polypeptide according to claim 1, wherein said administering induces production of an antibody that binds mammalian zona pellucida.

5. A method for inducing infertility in a mammal comprising administering to the mammal at least one polypeptide according to claim 1.

6. A method of inducing infertility in a mammal comprising administering at least one polypeptide according to claim 1, wherein said administering induces production of an antibody that binds mammalian zona pellucida.

7. The method of claim 4 wherein the mammal is cat.
8. The method of claim 5 wherein the mammal is cat.
9. The method of claim 6 wherein the mammal is cat.
10. The method of claim 4 wherein the mammal is dog.
11. The method of claim 5 wherein the mammal is dog.
12. The method of claim 6 wherein the mammal is dog.
13. The isolated polypeptide according to claim 1, said polypeptide comprising SEQ ID NO: 14.

14. The isolated polypeptide according to claim 1, said polypeptide comprising: a fragment SEQ ID NO: 14, where said fragment elicits an immune response to a polypeptide of SEQ ID NO: 14, said fragment comprising at least 20 contiguous amino acids of SEQ ID NO:14 from amino acid 1 to amino acid 116.

15. The isolated polypeptide according to claim 1, said polypeptide comprising: a fragment SEQ ID NO: 14, where said fragment elicits an immune response to a polypeptide of SEQ ID NO: 14, said fragment comprising at least 22 contiguous amino acids of SEQ ID NO: 14 from amino acid 1 to amino acid 116.

16. The isolated polypeptide according to claim 1, said polypeptide comprising: a fragment SEQ ID NO: 14, where said fragment elicits an immune response to a polypeptide of SEQ ID NO: 14, said fragment comprising at least 24 contiguous amino acids of SEQ ID NO:14 from amino acid 1 to amino acid 116.

17. The isolated polypeptide according to claim 1, said polypeptide comprising a fragment SEQ ID NO: 14, where said fragment elicits an immune response to a polypeptide of SEQ ID NO: 14, said fragment comprising at least 44 contiguous amino acids of SEQ ID NO:14 from amino acid 96 to amino acid 264.

18. The isolated polypeptide according to claim 1, said polypeptide comprising a fragment SEQ ID NO: 14, where said fragment elicits an immune response to a polypeptide of SEQ ID NO: 14, said fragment comprising at least 46 contiguous amino acids of SEQ ID NO:14.

19. The isolated polypeptide according to claim 1, said polypeptide comprising a fragment SEQ ID NO: 14, where said fragment elicits an immune response to a polypeptide of SEQ ID NO: 14, said fragment comprising at least 48 contiguous amino acids of SEQ ID NO:14.

* * * * *

UNITED STATES PATENT AND TRADEMARK OFFICE
CERTIFICATE OF CORRECTION

PATENT NO.        : 7,056,515 B2
APPLICATION NO. : 10/636620
DATED             : June 6, 2006
INVENTOR(S)       : Robert George Brown et al.

It is certified that error appears in the above-identified patent and that said Letters Patent is hereby corrected as shown below:

On the Title page, under item 56 Other Publications, --Kirkpatrick, J.F. et al., "Applications of pig zona pellucida immunocontraception to wildlife fertility control", J. Reprod. Fert. 1996, Supl. 50, pgs. 183-189-- was missing.

On the Title page, under item 57 Abstract, line 2, "…(ZP) polypeptide, and/or …" should be --…(ZP) polypeptide construct, and/or …--.

Column 5, line 14, "The polyoeotides of the…" should be --The polypeptides of the…--.

Columns 21 and 22, in the Sequence Listing, the first line "<160> NUMBER OF SEQ ID NOS: 16" should be --<160> NUMBER OF SEQ ID NOS: 17--

Columns 27 and 28, in the Sequence Listing, in SEQ ID NO: 7, "<213> ORGANISM: Mustela putorius furo" should be --<213>ORGANISM: dog--.

Columns 29 and 30, in the Sequence Listing, in SEQ ID NO: 8 "<213> ORGANISM: Mustela putorius furo" should be --<213>ORGANISM: dog--.

UNITED STATES PATENT AND TRADEMARK OFFICE
CERTIFICATE OF CORRECTION

PATENT NO.      : 7,056,515 B2                                          Page 2 of 2
APPLICATION NO. : 10/636620
DATED           : June 6, 2006
INVENTOR(S)     : Robert George Brown et al.

It is certified that error appears in the above-identified patent and that said Letters Patent is hereby corrected as shown below:

Columns 45 and 46, in Sequence Listing, at the line below the final "Phe" residue of SEQ ID NO: 16, the following Sequence SEQ ID NO: 17 was omitted:

```
-- <210>  SEQ ID NO 17
   <211>  LENGTH: 1793
   <212>  TYPE: DNA
   <213>  ORGANISM: cat <400>  SEQUENCE: 17
   caagtacagg tcttgcagcc agtggggctc ccgatggcat catgtggctg ctgcagcccc        60
   tcttgctctg tgttcccttg tctctcgctg tgcatggcca gcagaagccc caggtaccag       120
   attatcccgg tgaactccat tgtgggctcc agagccttca gtttgccata aacccgagcc       180
   ccgggaaagc gactcctgca ctcatagtct gggacaatcg cgggctgcca cacaagctgc       240
   agaacaactc tggctgcggt acctgggtaa gggagagccc gggggctcc gtgctgttag        300
   acgcctctta cagcagctgc tatgtcaacg agtgggtgag cacgacccaa tccccaggaa       360
   cgtcgaggcc ccccaccca gcatccaggg tgactcccca ggactcccac tacgtcatga        420
   tagtcggagt tgaaggcaca gatgcggctg ggcgcagggt taccaacacc aaggtgctca       480
   ggtgtcctag gaatccccca gaccaagctt tggtgtcgag cttaagtccc tctcctcttc       540
   aaaacgtagc actagaagct ccaaacgctg acttgtgtga ctctgtccca aagtgggaca       600
   ggcttccgtg tgcttcttca cccatcactc agggagactg caataagctt ggttgctgct       660
   acaaatcaga ggcaaattcc tgttactatg gaaacacagt gacctcacgc tgtacccaag       720
   acggccactt ctccatcgcc gtgtctcgga acgtgacctc accccactg ctcttaaatt        780
   ctctgcgctt ggccttcggg aaggaccgcg aatgtaaccc tgtgaaagca acacgtgcct       840
   ttgccctgtt cttttttcca tttaattcct gtggcaccac gagatgggtc actggagacc       900
   aggcagtata tgaaaatgag ctggtggcag ctagagatgt gagaacttgg agccatggtt       960
   ctattacccg tgacagtatc ttcaggcttc gagttagctg cagctactct gtaaggagta      1020
   atgccttccc gcttagcgtt caggtgttta ccatcccacc acccatctg aaaacccagc       1080
   atggaccct cactctggaa ctcaagattg ccaaagataa gcactatggc tcctactaca       1140
   ctattggtga ctacccagtg gtaaagttgc ttcgggatcc catttatgtg gaggtctcta      1200
   tccgccacag aacggacccc tccctgggc tgctcctcca taactgttgg gccacacccg       1260
   gcaagaactc ccagagtctg tcccagtggc ccattctggt gaaaggatgc ccctacgttg      1320
   gagacaacta tcaaaccaag ctgatccctg tccagaaggc tctggataca ccatttccat      1380
   cttactacaa gcgcttcagt attttcacct tcagctttgt ggacaccatg gcaaagtggg      1440
   cactcagggg accggtgtat ctgcactgta atgtatccat ctgccagcct gctgggacct      1500
   cctcctgtag gataacctgt cctgttgcca ggcgaagaag acactctgac ctccatcatc      1560
   acagcagtac tgcgagcatc tctagcaagg gtcccatgat tctactccaa gccactatgg      1620
   actctgcaga gaagctccac aaaaactcaa gttctcctat agactcccaa gctctgtgga      1680
   tggcaggcct ttccggggacc ctaatctttg gattcttgtt agtgtcctac ttggctatca     1740
   ggaaacggag gtgaattatt ccagttgtgt taataaaacc agattgcatt acc             1793 --
```

Signed and Sealed this

Nineteenth Day of June, 2007

JON W. DUDAS
*Director of the United States Patent and Trademark Office*